United States Patent
Hilgarth

(10) Patent No.: US 6,913,686 B2
(45) Date of Patent: Jul. 5, 2005

(54) METHODS FOR ANALYZING SOLDER PLATING SOLUTIONS

(75) Inventor: Monica K. Hilgarth, Oxford, CT (US)

(73) Assignee: Advanced Technology Materials, Inc., Danbury, CT (US)

(*) Notice: Subject to any disclaimer, the term of this patent is extended or adjusted under 35 U.S.C. 154(b) by 36 days.

(21) Appl. No.: 10/315,629

(22) Filed: Dec. 10, 2002

(65) Prior Publication Data

US 2004/0108224 A1 Jun. 10, 2004

(51) Int. Cl.$^7$ .............................................. G01N 27/416
(52) U.S. Cl. ............................... 205/788.5; 205/789.5; 204/405
(58) Field of Search .............................. 205/775, 778.5, 205/788.5, 789.5, 794; 204/405, 416, 434; 436/73

(56) References Cited

U.S. PATENT DOCUMENTS

| | | |
|---|---|---|
| 4,696,721 A | 9/1987 | Higashino et al. |
| 4,812,210 A | 3/1989 | Bonivert et al. |
| 5,286,358 A * | 2/1994 | Fletcher et al. ............. 205/780 |
| 5,324,400 A | 6/1994 | Eliash et al. |

FOREIGN PATENT DOCUMENTS

| | | |
|---|---|---|
| GB | 2327126 A | 1/1999 |
| JP | 56-55842 | 5/1981 |
| JP | 58-85140 | 5/1983 |
| JP | 06-265510 A | 9/1994 |

OTHER PUBLICATIONS

Konishi et al, Metal Finishing, Sep. 1966, pp. 66–69 and 75.*

Konishi et al, Kinzoku Hyomen Gijutsu, 17, 1966, pp. 5–12.*

CAPLUS abstract for Mladenovic et al, Glasnik Hemijskog Drustva Beograd, 35(4–6), 1970, pp. 353–358.*

Carlo Macca, et al. "pH–stat techniques in titrimetric analysis IV. pH–stat monitoring of chelatometric titration", Analytica Chimica Acta, 470, (2002) 277–288.

D. Midgley, et al., "Potentiometric Water Analysis" ISBN 0 47192983.2, p. 95 and pp. 145–153.

D. Midgley, et al., "Potentiometric Water Analysis" ISBN 0 47192983.2, p. 417.

D. Midgley, et al., "Potentiometric Water Analysis" ISBN 0 47192983.2, p. 120–124.

Document AP–471–1–D, Shipley.

Hanna Wikiel, et al., "On–Line Monitoring of Chemical Processes in Electronic Components Manufacturing", A paper presented at the CHIPCON '97 Conference Feb. 20–21, 1997, Sunnyvale Hilton Inn, Sunnyvale, CA, pp. 1–8.

Gallegos, Journal of Polymer Science, Sep. 1993, vol. 118, pp. 1137–1141.

J. Horkans, "Polargraphic methods of Monitoring Addition Agents in the Electroplating of Sn–Pb solders", 1998 IBM, 7 pgs. http://www.research.ibm.com/journal/rd/425/horkans.txt.

(Continued)

*Primary Examiner*—Kaj K. Olsen
(74) *Attorney, Agent, or Firm*—Yongzhi Yang; Margaret Chappuis; Steven J. Hultquist

(57) ABSTRACT

The present invention relates to methods and apparatus for determining concentrations of various inorganic or organic components in solder plating solutions, which include titration or parallel titration methods, direct potentiometry methods, calibration methods, and/or UV-Vis absorption analysis.

8 Claims, 22 Drawing Sheets

OTHER PUBLICATIONS

Scholz, E., Analysis of Fluoroborate Baths and other Fluoroborate Solutions, Galvanotechnik, 1975, 66(10), pp. 811–819 (abstract attached).

Skoog, D.A., Principles of Instrumental Analysis, $3^{rd}$ Ed., 1985, pp. 627–633.

Shipulo, et al., Potentiometric titration in analysis of electroplating baths, Zavodskaya Laboratoriya, 1991, 57(10), pp. 15–17 (abstract attached).

Caplus Abstract for Tsingarelli, et al., Solid–phase electrodes selective to lead and cadmium ions, Zhurnal Analiticheskoi Khimii, 1986, 41(3), pp. 449–452.

Caplus abstract for Adamova, et al., Determination of some surfactants by alternating current polarography, Biologicheski I Khimicheski Nauki, 1986, 1, pp. 73–76.

Caplus abstract for Miller R.L. LC methods development employing spectroscopy: analysis of electroplating solutions, Chromatography Newsletter, 1981, 9(1), pp. 10–12.

Halmekoski, J. Quantitative Spectrophotometric Determination of Catechol, Hydroquinone and Rescorcinol in Aqueous Solutions, J. Suomen Kemistilehti, 1959, 32, pp. 274–276.

Caplus abstract for Huang, et al., Determination of content and consuming rate of benzalacetone in AN electroplating bath, Cailiao Baohu, 2002, 35(8), pp. 49–50 (abstract attached).

* cited by examiner

METHODS FOR ANALYZING SOLDER PLATING SOLUTIONS

BACKGROUND OF THE INVENTION

1. Field of the Invention

The present invention relates to methods and apparatuses for analyzing the solder plating solutions, and more specifically to methods and apparatuses for determining concentration of various components in both eutectic solder plating solutions and high lead solder plating solutions.

2. Related Art

In the production of electrical printed circuit board, it is common to electroplate the electrically conductive regions of the board with a tin-lead coating, commonly referred to as solder. Such a tin-lead coating facilitates the subsequent connection of electrical components, such as resistors, transistors, integrated circuits, and the like, to the printed wiring board. Moreover, the increasing use of integrated circuits has necessitated use of multilayer printed wiring boards having solder plated through-holes for electrically connecting circuitry on the various layers of the board.

High-lead solder is also used to connect controlled collapsible chip contact ("C4 chip") to its substrate, for relieving thermal stress and providing a reliable contact between the chip and the substrate. C4 chips were intended for use in modules with low expansion substrates that minimize thermally generated stresses. These modules were often hermetically sealed to protect bare chips from the environment.

Eutectic solder solutions or high lead solder solutions commonly used for electrochemical deposition (ECD) of solder must be monitored in situ to insure optimal efficiency. Specifically, changes in the concentrations of inorganic components (such as acid, lead, and tin) and organic additives (such as polymeric non-ionic surfactant, brightener, and antioxidant) in such solder solutions must be determined during the solder plating process for accurate and precise process control.

However, conventional methods for determining component concentrations in solder plating solutions are complicated and unreliable, resulting in high error rates. Moreover, no automated, on-line solder analytical tools are currently available for automatic concentrations analysis of solder plating solutions, and most of the solder plating solution analyses are still conducted manually.

Moreover the final processing of highly complex and expensive microcomputer chips by solder plating demands rigorous control of the bath.

It is therefore an object of the present invention to provide methods for faster and more accurate determination of component concentrations in solder plating solutions.

It is another object of the present invention to provide automated, on-line analytical tools for automatic concentration analysis of solder plating solutions, and more preferably an integrated analytical tool for automatic determination of the concentrations of all the inorganic and organic components of a sample solder plating solution.

Other objects and advantages will be more fully apparent form the ensuing disclosure and appended claims.

SUMMARY OF THE INVENTION

The present invention in one aspect relates to a method for determining concentration of an acid contained in a sample solder plating solution, comprising the steps of:

(a) measuring electropotential responses of one or more calibration solutions of known acid concentrations;

(b) determining the correlation between acid concentrations and electropotential responses of solutions, based on the calibration measurements;

(c) measuring electropotential response(s) of the sample solder plating solution; and (d) determining acid concentration in the sample plating solution, based on the electropotential response(s) measured in step (c) and the correlation determined in step (b).

The present invention in another aspect relates to a method for determining concentration of an acid contained in a sample solder plating solution, comprising the steps of:

(a) providing a sample solder plating solution with an unknown acid concentration;

(b) titrating said sample solder plating solution, using a base titrant;

(c) monitoring pH value of the sample solder plating solution during the titration process and terminating the titration process when a predetermined endpoint is reached, wherein the pH value of the sample solder plating solution at the predetermined endpoint is in a range of from about 3.5 to 4.5;

(d) recording the total amount of base titrant used for reaching the predetermined endpoint;

(e) optionally, determining the amount of titrant that reacts with tin ions in the sample solder plating solution to form an insoluble tin compound; and (f) calculating the acid concentration in the sample solder plating solution, based on the total amount of titrant used, and optionally, based on the amount of titrant that has reacted with tin ions therein.

The present invention in a further aspect relates to a method for determining tin concentration in a sample solder plating solution comprising tin and lead ions, by titrating the sample solder plating solution with a titration solution that comprises a material selected from the group consisting of iodine and iodide, and by measuring reduction-oxidation potential responses of such sample solder plating solution, during the titration.

Note that the term "tin ions" described herein refers only to the two-valence Sn(II) ions, not the four-valence Sn(IV) ions, unless otherwise specified.

The present invention in a still further aspect relates to a method for determining lead concentration in a sample solder plating solution that comprises tin and lead ions, comprising the steps of:

(a) determining the total metal concentration in the sample solder plating solution;

(b) determining the tin concentration in such sample solder plating solution, as described hereinabove;

(c) calculating the lead concentration in the sample solder plating solution, by subtracting the tin concentration from the total metal concentration.

The present invention in still another aspect relates to a method for determining lead concentration in a sample solder plating solution, comprising the steps of:

(a) measuring electropotential responses of one or more calibration solutions of known lead concentrations;

(b) determining the correlation between lead concentrations and electropotential responses of solutions, based on the calibration measurements;

(c) measuring electropotential response(s) of the sample solder plating solution; and (d) determining lead concentration in the sample plating solution, based on the electropotential response(s) measured in step (c) and the correlation determined in step (b).

The present invention further relates to a method for determining lead concentration in a sample solder plating solution, comprising the steps of:

(a) adjusting pH value of the sample solder plating solution to a base value in a range of from about 4 to about 4.5;

(b) titrating the sample solder plating solution by adding successive volumes of a primary titration solution comprising EDTA thereinto;

(c) concurrently to step (b), monitoring the pH value of the sample solder plating solution after addition of each volume of the primary titration solution, and whenever a pH drop is observed in the sample solder plating solution, a sufficient volume of a secondary titration solution is added into the sample solution, so as to adjust the pH value of the sample solution back to the base value before addition of next volume of the primary titration solution;

(d) terminating the titration process at an end point, where further addition of the primary titration solution no long causes pH drop in the sample solder plating solution;

(e) recording total volume of the secondary titration solution used, and optionally total volume of the primary titration solution for reaching the titration end point; and (d) determining the lead concentration in said sample solder plating solution, based on the total volume of the secondary titration solution used;

(e) optionally, determining the total metal concentration in the sample solder plating solution, based on the total volume of the primary titration solution for reaching the titration end point.

A still further aspect of the present invention relates to a potentiostatic method for determining concentration of polymeric non-ionic surfactant in a sample solder plating solution, by measuring:

(a) time required for occurrence of an unlimited increase in plating current; or (b) analytical signal selected from the group consisting of plating current and stripping charge, as measured during the occurrence of an unlimited increase in plating current.

A yet another aspect of the present invention relates to a potentiometric titration method for determining concentration of polymeric non-ionic surfactant in a sample solder plating solution, comprising the steps of:

(a) titrating the sample solder plating solution by adding a titration solution thereinto, so as to form an insoluble reaction product with the lead-polymeric non-ionic surfactant complex in said sample solution;

(b) detecting a titration end point for the sample titration process in step (a), and recording the amount of titration solution used for reaching such titration end point;

(c) providing multiple standard solder plating solutions containing polymeric non-ionic surfactant at unique, known concentrations;

(d) titrating the multiple standard solder plating solutions by using the titration solution, and detecting a titration end point for each of the multiple standard solder plating solutions;

(e) calculating an empirical titration factor that correlates volume of the titration solution used with polymeric non-ionic surfactant concentrations in the standard solder plating solutions; and (f) determining the polymeric non-ionic surfactant concentration in the sample solder plating solution, based on the volume of the titration solution recorded in step (b) and the empirical titration factor calculated in step (e).

A still further aspect of the present invention relates to a method for determining concentration of brightener in a sample solder plating solution, by obtaining a UV-Vis absorption spectrum for the sample solder plating solution, determining the absorbance of the sample solder plating solution at a wavelength in a range of from about 393 nm to about 413 nm, and calculating the brightener concentration in the sample solder plating solution, based on the absorbance at such wavelength.

A still further aspect of the present invention relates to a method for determining concentration of antioxidant in a sample solder plating solution, comprising the steps of:

(a) adding an acid solution into the sample solder plating solution for increasing pH value of the sample solder plating solution to a predetermined level;

(b) monitoring oxidation-reduction potential of the sample solder plating solution before and after the addition of the acid solution;

(c) constructing an oxidation-reduction potential response curve, by plotting the oxidation-reduction potential measured for such sample solder plating solution as a function of the pH value; and (d) determining the concentration of antioxidant concentration in the sample solder plating solution, by analyzing the oxidation-reduction potential response curve of the sample solder plating solution.

A still further aspect of the present invention relates to a method for determining concentration of antioxidant in a sample solder plating solution, comprising the steps of forming a derivative of the antioxidant that is detectable by UV-Vis spectroscopy, and conducting UV-Vis absorption analysis at a wavelength that maximizes UV absorbance of such derivative of the antioxidant, so as to determine the antioxidant concentration in the sample solder plating solution.

A still further aspect of the present invention relates to a method for determining concentration of antioxidant in a sample solder plating solution, comprising the steps of directly conducting UV-Vis absorption analysis of the solder plating solution at a wavelength that maximizes UV absorbance of the antioxidant, and determining the antioxidant concentration in the sample solder plating solution based on the UV-Vis absorption analysis result.

A still further aspect of the present invention relates to an optical cell for conducting spectrometric analysis of one or more test solutions, comprising:

a first fluid compartment of a first volume;

one or more fluid inlets connected to the first fluid compartment for introducing one or more test solutions thereinto;

a second fluid compartment of a second volume connected to the first fluid compartment, wherein the second volume is smaller than the first volume;

a fluid outlet connected to the second fluid compartment for discharging the one or more test solutions;

optionally, a fluid mixing device in the first and/or second fluid compartment for mixing the one or more test solutions;

an irradiation light source for irradiating light into the second fluid compartment;

a light detector coupled with the irradiation light source for detecting light transmitted or emitted by the one or more test solutions in the second fluid compartment; and optionally, a computational device connected with the light detector, for collecting absorbance spectrum of such one or more test solutions and conducting spectrometric analysis based thereon.

A still further aspect of the present invention relates to a method for determining concentration of a component in a sample solder plating solution, based on Raman spectroscopic analysis.

Additional aspects, features and embodiments of the invention will be more fully apparent from the ensuing disclosure and appended claims.

DETAILED DESCRIPTION OF THE INVENTION, AND PREFERRED EMBODIMENTS THEREOF

Figure 1:
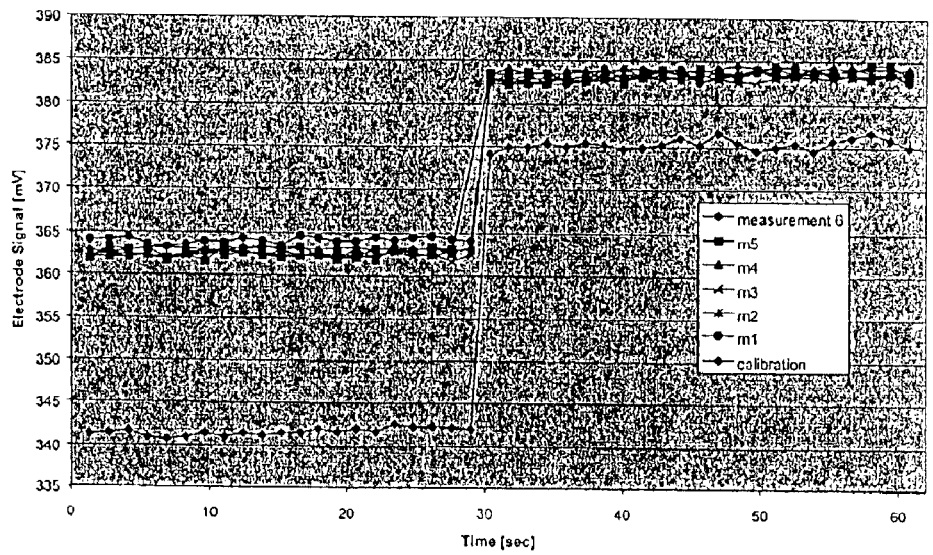
FIG. 1 is a graph that shows the electropotential responses of a solution before and after addition of a sample methanesulfonic acid solution, according to six measurements thereof, as well as the electropotential response of a solution before and after addition of a calibration methanesulfonic acid solution.

The present invention proposes various methods and apparatuses for automated analysis of the inorganic components (including acid, tin, and lead) and organic components (including polymeric non-ionic surfactant, brightener, and antioxidants) concentration in a sample solder plating solution (i.e., eutectic or high lead solder plating solution), as described in detail in the following sections.

Total Acid Analysis

Acid-base titration methods have been conventionally used for determining the total acid (i.e., methanesulfonic acid) concentration in solder plating solutions, by titrating the sample solder plating solution with a base titrant, so as to reach a titration endpoint where all the methanesulfonic acid (MSA) has been neutralized by the base titrant. The endpoint is usually indicted by a change of color exhibited by the phenolphthalein pH indicator contained by the sample solution.

Phenolphthalein shows color change when the pH is near or above 8.0. However, when the pH value of the sample solder plating solution being titrated rises, the dissolved metal components, such as $Sn^{2+}$ and $Pb^{2+}$, persistently precipitate out of the sample solution, regardless of the variety of titrants (for example, hydroxides, carbonates, and amines), buffers, or electrolytes used. Such precipitation of the metal components causes errors in the conventional acid-base titration methods, because when the $Sn(OH)_2$ and $Pb(OH)_2$ precipitates form, more titrant is required in order to reach the endpoint, resulting in an MSA concentration reading that is higher than the actual MSA concentration. Tin ($Sn^{2+}$) is particularly sensitive to formation of hydroxide, which already starts at low pH values (i.e., pH>1), whereas lead solutions can be titrated as far as pH 7 before any hydroxide precipitation starts.

In order to avoid the above-described problem associated with conventional acid-base titration methods, the present invention proposes the following new methods for total acid concentration determination:

I. Direct Potentiometric Methods

The direct potentiometry techniques proposed by the present invention involves direct measurement of the electropotential of the sample solder plating solution, and determination of total acid concentration in such sample solder plating solution, based on the electropotential measurement.

Specifically, the present invention determines the total acid concentration in a sample solder plating solution, by the following steps:

(a) providing one or more calibration solutions containing methanesulfonic acid at known, distinctive concentrations;

(b) measuring electropotential responses of such calibration solutions and determining correlation between acid concentrations and electropotential responses, based on the calibration measurements;

(c) measuring electropotential response(s) of the sample solder plating solution; and (d) determining acid concentration in said sample plating solution, based on the electropotential response(s) measured in step (c) and the correlation determined in step (b).

The sample solder plating solution is preferably diluted before any measurement is conducted. The purpose of diluting the sample solder plating solution is to bring the pH value of such solution in a range of from about 1 to 3, preferably near 2 (7 mM). At this pH level, there is no hydrolysis of metal ions in the sample solution, and the potential response measured by the glass electrode is Nernstian, which increases the reliability of the electropotential measurement. For example, the sample solution may be diluted by adding the sample solution (for example 1 or 2 ml) into deionized water (for example, 50 or 100 ml), or deionized water that contains 15 to 25% $KNO_3$ by volume. The $KNO_3$ is used herein as an ionic strength buffer, for minimizing interference from tin and lead during acid concentration determination.

(A). Direct Potentiometry Based on Standard Addition:

One specific embodiment of the direct potentiometry proposed by the present invention uses the following steps for determining the acid concentration in a sample solder plating solution:

A slope k was first determined, by measuring the electropotential responses of two successive standard additions of an acid concentrate (with known acid concentration therein) into deionized water (preferably deionized water containing 20% potassium nitrate by volume), according to the following equation:

$$k = \frac{E_{ii} - E_i}{\log 2}$$

Wherein $E_{ii}$ is the electropotential response measured after introduction of the second standard addition of the acid concentrate into the deionized water, and $E_i$ is the electropotential response measured after introduction of the first standard addition of the acid concentrate into the deionized water.

Slope k so determined is indicative of the correlation between acid concentration and electropotential response in a solution.

The electropotential of the sample solder plating solution can then be measured, using a glass electrode. It is preferred that the sample solder plating solution is diluted before the electropotential measurement. For example, the sample solution can be diluted ⅕₀, using deionized water (preferably deionized water containing 20% $KNO_3$ by volume).

Next, a standard addition of acid concentrate is added into the diluted sample plating solution, and the electropotential of the sample solder plating solution with the standard addition is measured. Preferably, the amount of standard addition is controlled in such manner that the estimated acid concentration in the diluted sample solution is approximately doubled due to such standard addition.

The concentration of total acid in the sample solder plating solution can then be calculated, according to the following simplified equation:

$$C_a = \frac{V_A c_A}{V_s[\text{antilog}((E_2 - E_1)/k) - 1]}$$

Wherein $C_a$ is the concentration of acid in the sample solder plating solution, $V_A$ is the volume of the standard addition of acid concentrate added into the sample solder plating solution, $c_A$ is the concentration of acid in the standard addition, $V_S$ is the volume of the diluted sample soldering plating solution, $E_1$ and $E_2$ are the potential responses of the diluted sample plating solution measured before and after and the standard addition, respectively.

The above-described method for determining total acid concentration in solder plating solutions is generally characterized by a relative standard deviation of less than ±5%, and more specifically less than ±1.5%.

(B). Direct Potentiometry Based on Potential Increases:

Another specific embodiment of the potentiometric method proposed by the present invention uses the following steps for determining the acid concentration in a sample solder plating solution:

A predetermined electrical current is passed between two Pt electrodes that are submerged in a base solution, wherein the base solution contains all the components of the sample solder plating solution to be measured, except the methanesulfonic acid. The electropotential between such two Pt electrodes is measured. Usually, the electropotential between the two Pt electrodes is monitored for a sufficient period of time (for example 20 to about 40 seconds, more preferably about 30 seconds), so that the two Pt electrodes reach an equilibrium state with more reliable electropotential reading.

A certain amount of the sample solder plating solution to be measured is then added into the base solution.

The predetermined electrical current is again passed between the two Pt electrodes, and the electropotential of the base/sample solution is measured.

As shown in FIG. 1, the electropotential measured after the addition of the sample solution into the base solution shows a substantial increase in comparison with that measured before the addition of the sample solution.

Such increase in electropotential is proportional to the acid concentration in the sample solution and can be used to determine the acid concentration in the sample solution. For example, calibration solutions containing the methanesulfonic acid at known, distinctive concentrations can be prepared, and the electropotential increases caused by addition of such calibration solutions are measured, so as to construct a calibration curve showing the electropotential increases as a function of the acid concentrations in solder plating solutions.

FIG. 1 shows multiple electropotential response curves, six of which were measured for a sample solder plating solution, and one was measured for a calibration solution, according to the method described hereinabove.

It is evident from FIG. 1 that the electropotential responses measured for the sample solder plating solution is highly reproducible, and the electropotential increases exhibited by each sample measurement are consistent. By comparing the electropotential increase caused by addition of the sample plating solution with the electropotential increase caused by the calibration solution, one can determine the acid concentration in a sample solder plating solution.

The following table shows six measurements of methanesulfonic acid concentration in a sample solution, determined according to the above-described techniques based on electropotential increases:

TABLE 1

| Experiment # | Methanesulfonic Acid Concentration Measured (g/L) |
|---|---|
| 1 | 5.226009 |
| 2 | 4.689542 |
| 3 | 4.61905 |
| 4 | 4.605715 |
| 5 | 4.72701 |
| 6 | 4.598907 |
| Average | 4.65 |
| Standard Deviation | 0.05 |
| Relative Standard Deviation | 1.10% |

II. Incomplete Titration

The incomplete titration technique used by the present invention for determining the total acid concentration in a sample solder plating solution involves arbitrary selection of a titration endpoint having a pH value in a range of from about 3.5 to about 4.5, more preferably in a range of from about 3.8 to about 4.4, and most preferably a pH value of about 4.

Specifically, the incomplete titration technique of the present invention comprises the following steps:

(a) providing a sample solder plating solution having an unknown acid concentration;

(b) titration such sample solder plating solution, using a base titrant;

(c) continuously monitoring pH value of such sample solder plating solution during the titration process, by using a pH probe;

(d) terminating the titration process when a predetermined endpoint is reached, wherein at such predetermined endpoint, the pH value of the sample solder plating solution is in a range of from about 3.5 to about 4.5;

(e) recording the total amount of titrant used for reaching the predetermined endpoint;

(f) optionally, determining the amount of titrant that has reacted with tin ions in such sample solder plating solution to form an insoluble tin compound; and (g) calculating the acid concentration in the sample solder plating solution, based on the total amount of titrant used, and optionally, based on the amount of titrant that has reacted with tin ions therein.

The base titrant that can be used for practicing the incomplete titration method as described hereinabove includes, but is not limited to, NaOH, KOH, and ethanolamine.

The incomplete titration method of the present invention distinguishes over conventional acid-based titration methods, by selecting a titration endpoint, at which most of the methanesulfonic acid in the sample solder plating solution has reacted with the strong base titrant and therefore recovered, but the lead ions in such sample solder plating solution have not started precipitate yet. Instead of allowing the titration process to be carried on all the way to the conventional endpoint, at which the pH value of the sample solder plating solution reaches about 7 and at which the lead ions in the solution starts to precipitate and causes measurement error, the incomplete titration method of the present invention terminates the titration process at such a selected endpoint defined by a pH value in a range of from about 3.5 to about 4.5, so as to maximize the recovery of the methanesulfonic acid, while concurrently minimizing precipitation of the lead ions in the sample solder plating solution during the titration.

The selected titration endpoint according to the present invention is preferably characterized by a pH value of sample solder plating solution in the range of from about 3.8 to about 4.4, and more preferably about 4.

At pH 4, more than 99% of the methanesulfonic acid in the sample solder plating solution has reacted with the strong base titrant and therefore recovered, but the lead ions have not started precipitating out of the solution, and the titration process therefore does not suffer from lead interference.

Since tin ions in the sample solder plating solution to be titrated have a high affinity for hydroxide, even at pH value of 2, the tin ions ($Sn^{2+}$) inevitably react with the strong base titrant to form tin hydroxide ($Sn(OH)_2$) precipitate, therefore affecting the base titrant consumption. However, the effect of tin ions can be readily corrected, because the consumption of hydroxide in the formation of $Sn(OH)_2$ precipitate is stoichiometric, according to the following chemical reaction:

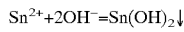

$$Sn^{2+} + 2OH^- = Sn(OH)_2 \downarrow$$

Therefore, by determining the amount of tin ions in the sample solution according to methods described hereinafter, one can readily determine the amount of titrant consumed by the tin ions alone, and subtract such from the total amount of titrant used, so as to obtain the amount of titrant used for neutralizing and recovering the methanesulfonic acid in the sample solder plating solution.

Figure 2:
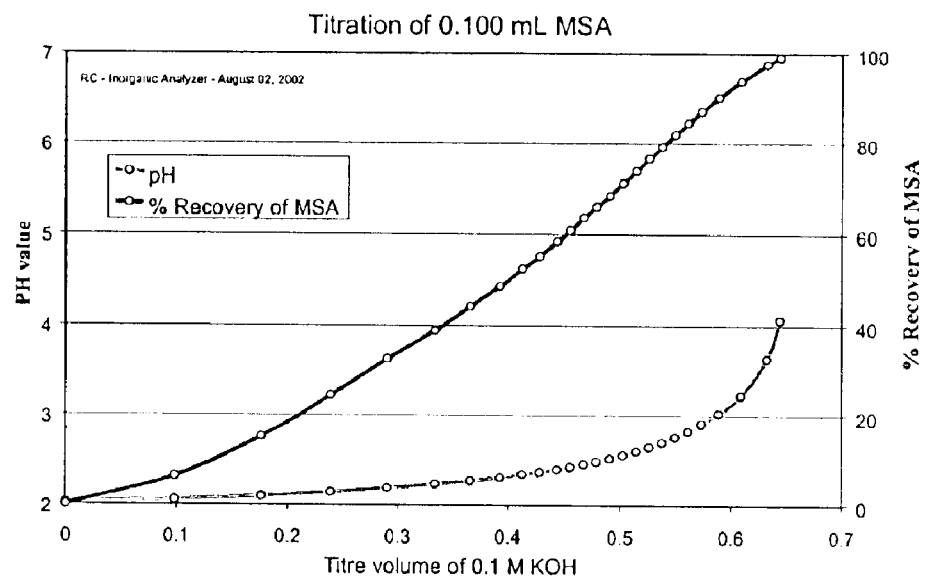
FIG. 2 is a titration curve for the methanesulfonic acid (MSA), measured during an titration process using 0.1M KOH as titrant, and plotting the pH or recovery percentage of the MSA as a function of the volume of the KOH titrant added.

FIG. 2 shows a titration curve for the methanesulfonic acid, measured during an incomplete titration process of the present invention, as described hereinabove. It is evident that the more KOH titrant is added into the sample solder plating solution, the greater the recovery of the methanesulfonic acid. At pH 4, the methanesulfonic acid recovery rate is about 99%.

Total acid analysis was conducted using the incomplete titration method described hereinabove. Three standard solutions containing methanesulfonic acid at various known concentrations were tested, and the test results are as follows:

TABLE 2

Total Acid Analysis Results Using Incomplete Titration

| | Standard Solution | | |
|---|---|---|---|
| | #1 | #2 | #3 |
| Concentration (g/l) | 50 | 60 | 70 |
| Measurement | 50.52 | 60.00 | 69.93 |
| Results (g/l) | 50.65 | 60.39 | 69.76 |
| | 50.88 | 60.27 | 70.08 |
| | 49.90 | 60.22 | 69.95 |
| | 50.71 | 60.13 | 69.80 |
| Average | 50.53 | 60.20 | 69.90 |
| % Std. Dev. | 0.74% | 0.24% | 0.18% |

TIN ANALYSIS

The present invention determines the tin concentration in a sample solder plating solution that comprises both tin and lead ions, by an oxidation-reduction potential (ORP) titration process, which comprises the steps of titrating such sample solution with a titrant solution, and monitoring the ORP response of the sample solder plating solution during the titration.

Various titration solutions can be used, for generating an ORP response that is indicative of the tin concentration in the sample solution. Preferably, such titration solution comprises either iodine or iodide.

I. Iodine Titration Using Stabilizing Solution

One specific embodiment of the present invention relates to determination of tin concentration in a sample solder plating solution using iodine titration techniques, which comprises the following steps:

(a) adding a stabilizing solution into the sample solder plating solution, to stabilize the lead ions therein to prevent precipitation of the lead ions during subsequent titration;

(b) titrating the sample solder plating solution with a titration solution comprising iodine;

(c) monitoring oxidation-reduction potential of the sample solder plating solution during the iodine titration, for determining an end point of the titration process; and (d) calculating the tin concentration in the sample solder plating solution, based on the titration end point determined in step (c).

Preferably, the sample solder plating solution is first diluted in deionized water before the stabilizing solution is added.

The stabilizing solution used by the present invention may comprise ethylenediaminetetraacetate (EDTA) which complexes with the lead ions in the solder plating solution, so as to keep the lead ions from precipitating with iodine during the subsequent iodine titration. The stabilizing solution preferably comprises both EDTA and ammonia acetate, wherein ammonia acetate functions to adjust the pH value of the sample solder plating solution to above 4, so that the lead ions therein will effectively complex with EDTA.

Subsequently, the tin ions in the diluted sample solder plating solution are titrated with a titration solution comprising iodine. The tin ions in the solder plating solution undergo the following oxidation-reduction reaction with the iodine in the titration solution:

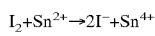

$$I_2 + Sn^{2+} \rightarrow 2I^- + Sn^{4+}$$

Therefore, the oxidation-reduction potential (ORP) of the sample solder plating solution can be readily monitored, by using a ORP electrode during the iodine titration process, for the purpose of determining an end point of the titration, where all the +2 tin ions in the solder plating solution haven oxidized to the +4 valence.

Knowing the volume and iodine concentration of the titration solution used to reach such end point, one can readily determine the amount of tin ions in the sample solder plating solution.

Usually, for analyzing the tin concentration in a eutectic solder plating bath, 1 ml sample is needed to conduct the iodine titration analysis, and for a high lead solder plating bath, 5 ml sample is needed. The iodine solution may also comprise a small amount of potassium iodide (KI), for purpose of preserving the iodine therein.

The lead ions in the sample solder plating solution are stabilized by using EDTA or EDTA/acetate buffer, which complexes with the lead ions in the solder plating solution, so as to keep the lead ions from precipitating with iodine during the subsequent iodine titration.

Figure 3:
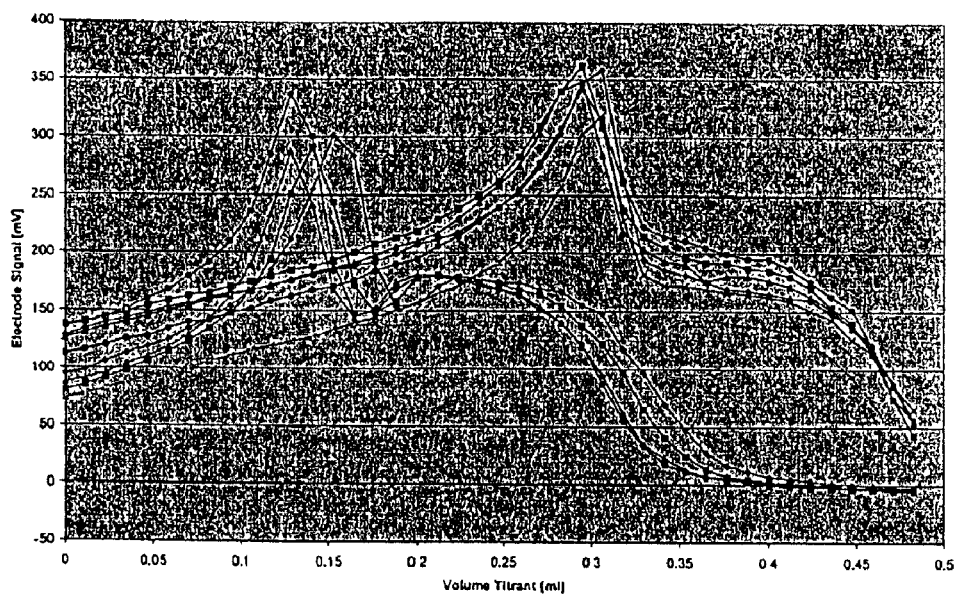
FIG. 3 is a graph that plots the electropotential of a sample solder plating solution as a function of the volume of iodine titrant added into such sample solution, according to the iodine titration method for tin analysis.

Examples of multiple iodine titration response curves are shown in FIG. 3. These titration response curves were constructed for multiple solder plating solutions, which contain tin at concentrations either above or below the ideal control point (approximately 3.10 g/L) in a high lead solder plating solution. On such iodide titration curves, when $dV/dVol_{Titrant}=0$, which is reflected by an inflection point on the titration curve, the reaction between $Sn^{+2}$ and $I_2$ is complete. Therefore, knowing the volume of the iodine titration solution used at such inflection point, we can determine the total amount of tin ions in the sample plating solution. Note that a second inflection point appears approximately 0.05 ml after the first inflection point, which may be caused by reaction of the antioxidant or brighteners of the sample solution with iodine.

In one preferred embodiment, the present invention employs dual polarized platinum electrodes for detecting the titration endpoint during such iodine titration process.

The use of the dual platinum electrodes in the present invention solves the electrode passivation problem commonly seen in systems using other types of electrodes, by facilitating automatic in-line cleaning of the analytical cell and the electrodes via an electrolysis process in a conducting electrolyte.

Figure 4A:
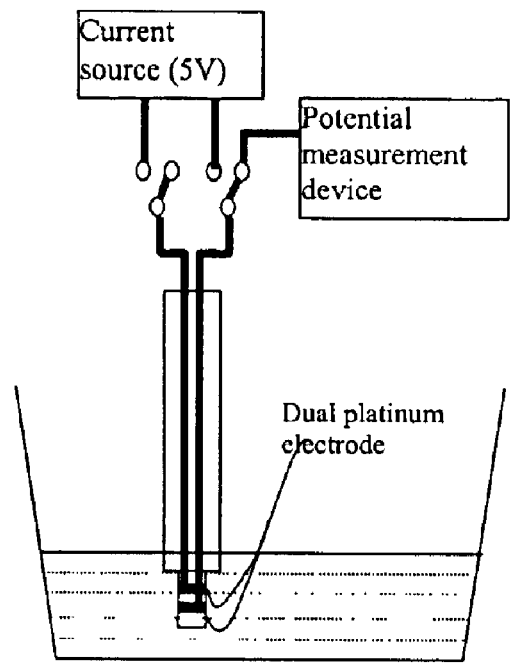
FIGS. 4A and 4B show dual platinum electrodes for measuring oxidation-reduction potential of the sample solder plating solution, according to one embodiment of the present application.
Figure 4B:
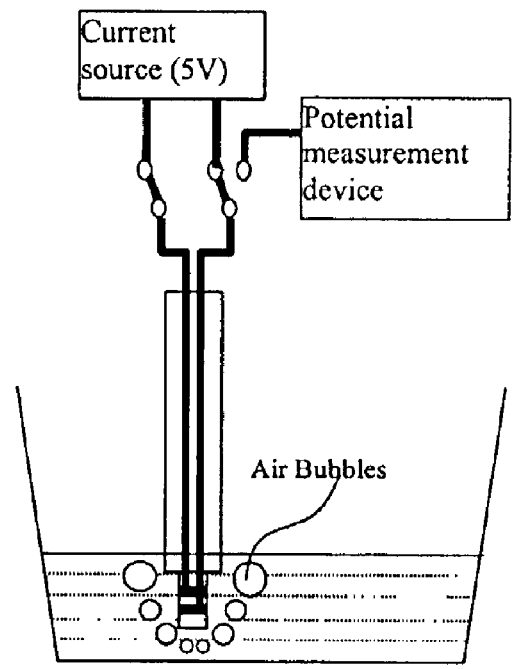

Specifically, dual platinum electrodes as those show in FIGS. 4A and 4B of the present application can be used, which include a first electrode that can be connected to a potential measurement device and functions as the oxidation-reduction potential (ORP) electrode, and a second, auxiliary electrode used solely for electrolytic gas generation. Under normal conditions, the first electrode is connected to the potential measurement device for ORP measurements of the sample solder plating solutions, as shown in FIG. 4A. During ORP measurement intervals, the first electrode is disconnected from the potential measurement device, and connected to a current source (with an operating voltage of about 5–12 VAC), together with the second, auxiliary electrode, as shown in FIG. 4B. Both the first and the second electrodes are then immersed in a conducting electrolyte solution. Electrical current passes through the first and second electrodes and the electrolyte solution, generating gases (shown as air bubbles in FIG. 4B) and providing a vigorous surface process which peals away any deposit on the electrode surface that may passivate the electrode response to the electropotential changes.

Figure 5:
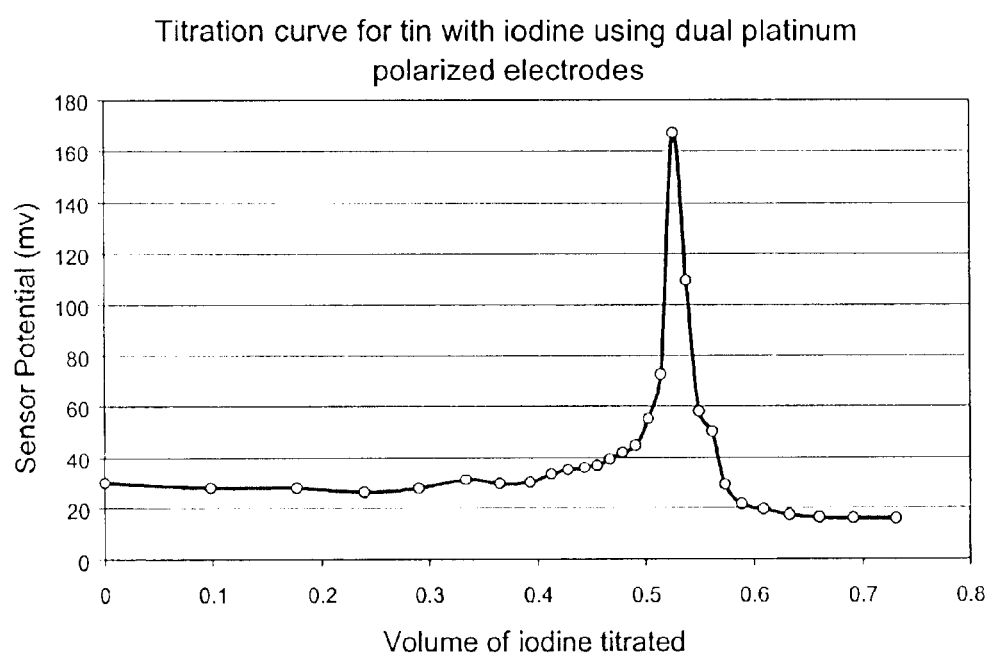
FIG. 5 is a titration curve for iodine titration of tin ions, using dual platinum polarized electrodes.

FIG. 5 shows a titration curve measured for iodine titration of tin ions using the dual platinum electrodes as described hereinabove. The ORP response shows a readily determinable titration endpoint.

II. Iodine Titration with Pre-Titration Removal of Lead Ions

Another specific embodiment of the present invention relates to iodine titration techniques with pre-titration removal of lead ions from the sample solder plating solution, which comprises the following steps:

(a) adding a lead-precipitating agent into the sample solder plating solution, for forming an insoluble compound with the lead ions therein, so as to remove the lead ions from said sample solder plating solution;

(b) titrating the sample solder plating solution with a titration solution comprising iodine;

(c) monitoring oxidation-reduction potential of the sample solder plating solution during the iodine titration, for determining an end point of said titration; and (d) calculating the tin concentration in the sample solder plating solution, based on the titration end point determined in step (c).

Preferably, the sample solder plating solution is first diluted in deionized water before the lead-precipitating agent is added.

The lead-precipitating agent used by the present invention may comprise any chemical compound that reacts with the lead ions in the sample solder plating solution to form an insoluble precipitate, provided that such chemical compound does not cause precipitation of the tin ions and has little or no effect on the tin titration result. Preferably, such lead-precipitating agent is selected from the group consisting of HCl, NaCl, KCl, and mixtures thereof. More preferably, such lead-precipitating agent comprises hydrochloric (HCl) acid in a solution at a concentration of from about 20% to about 45% by weight, and most preferably at a concentration of from about 35% to about 40% by weight. Such lead-precipitating agent may also comprises potassium or sodium chloride (KCl or NaCl) in a solution at a concentration of from about 1M to about 3M, and more preferably at a concentration of about 2M.

Figure 6:
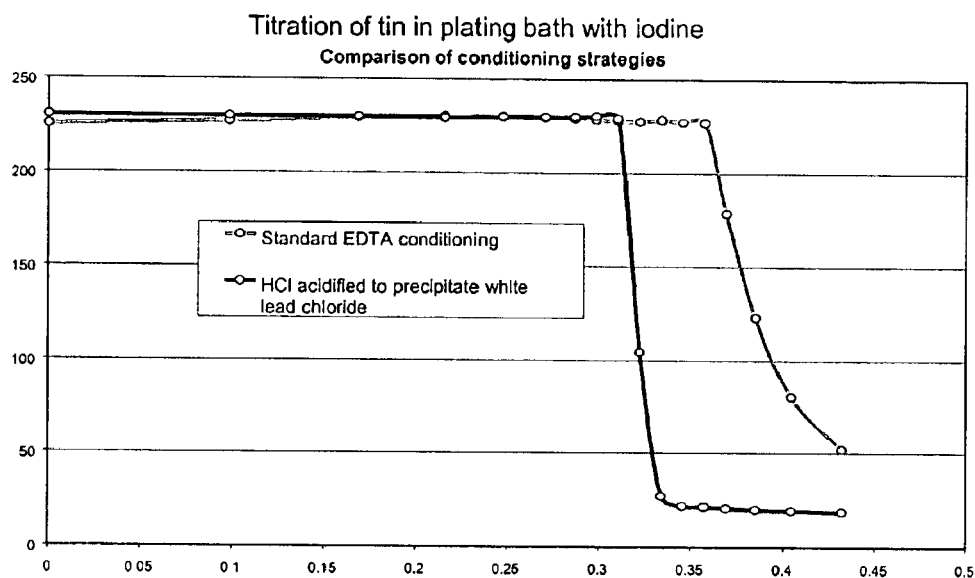
FIG. 6 is an iodine titration curve of tin, in which HCl is used to remove lead ions from the sample solution before the titration process, in comparison to an iodine titration curve where EDTA is used for stabilizing the lead ions.

FIG. 6 shows an iodine titration curve of tin using HCl to remove lead ions from the sample solution before the titration process, in comparison to an iodine titration curve where EDTA is used for stabilizing the lead ions.

Figure 7:
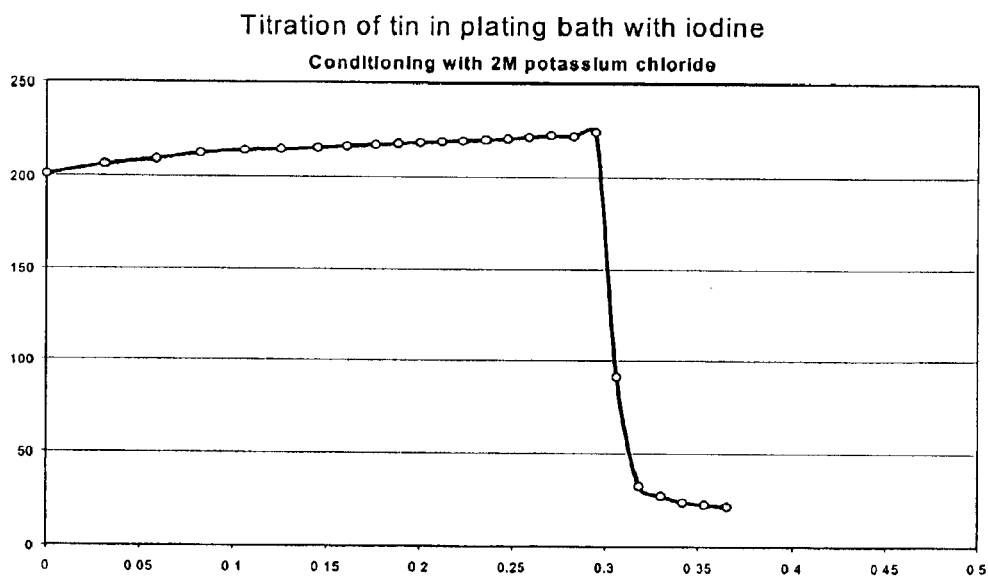
FIG. 7 is another iodine titration curve of tin, in which KCl is used to remove lead ions from the sample solution before the titration process.

FIG. 7 shows another iodine titration curve of tin, using KCl to remove lead ions from the sample solution before the titration process.

By removing the lead ions from the sample solder plating solution before the iodine titration, the titration result shows greater reproducibility and linearity, with less requirements for electrode cleaning.

Figure 8:
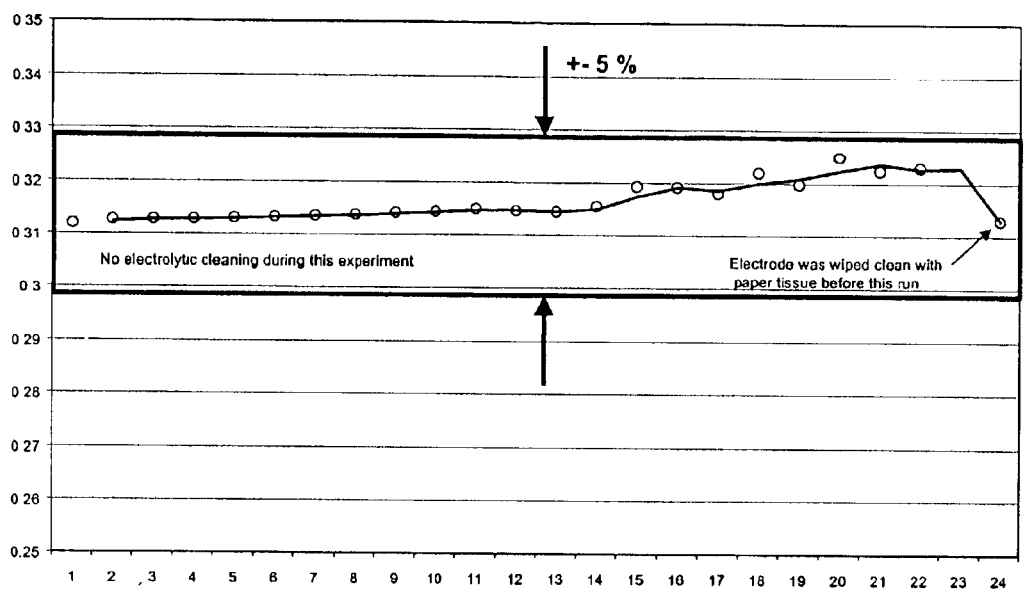
FIG. 8 shows the results of a series of 24 iodine titrations for tin analysis, conducted with the pre-titration removal of lead ions.

FIG. 8 shows the results of a series of 24 tin iodine titrations, which were conducted with the pre-titration removal of lead ions, as described hereinabove. The overall standard deviation was about 5%. No cleaning of the ORP electrode was conducted during these titration runs. However, after 14 runs, the titration results started to gradually deviate from the original titration results, which indicates that the ORP needs to be cleaned after about 14 titrations. After about 22 titration runs, the ORP electrode was cleaned with a paper tissue, while the titration result immediately returned to the level of the original titration results.

Figure 9:
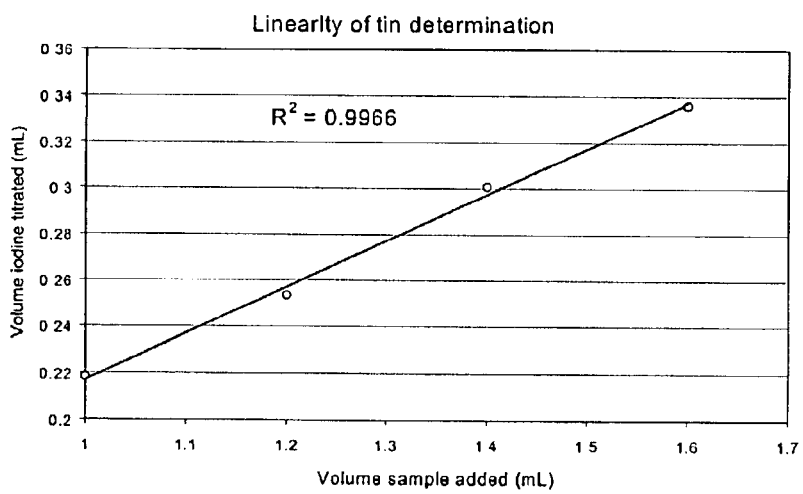
FIG. 9 shows a linear curve connecting four iodine titration results for tin analysis, with pre-titration removal of lead ions.

FIG. 9 shows the linearity of four iodine titration results with pre-titration removal of lead ions as described hereinabove, using the ramp function. Good linearity was shown between the volume of sample solder plating solution added and the volume of iodine titrant used.

Lead Analysis

I. Subtraction Method

Lead concentration determination can be conducted indirectly, by first determining the total metal concentration in a sample solder plating solution, and then determining tin concentration in such sample solution, using methods described hereinabove, so that lead concentration can be determined by subtracting the tin concentration from the total metal concentration.

The total metal concentration can be determined by a titration method.

Specifically, an excess amount of complexing agent (such as EDTA) is added into a preferably diluted sample solder plating solution, in which such complexing agent forms complexes with the metal ions (i.e., both tin and lead ions). Preferably, an EDTA/ammonia acetate solution is used as the complexing agent, so that the EDTA forms complexes with the tin and lead ions, and the ammonia acetate adjusts the pH value of the solution to above 4.

Excess EDTA in the sample solder plating solution, which is not complexed with the metal ions, is then titrated, by using a titration solution, which preferably comprises copper sulfate. The $CuSO_4$ titration can be monitored using a sensor, such as an ion selective electrode (ISE), a photometric sensor, or a thermometric sensor, etc., for determining the titration end point wherein all the excess EDTA is consumed by copper sulfate.

The amount of copper sulfate used in the titration is then subtracted from the total amount of EDTA added, to yield the amount of EDTA that has actually complexed with tin and lead ions in the sample solder plating solution, for determining the total metal concentration in the sample solder plating solution.

The concentration of tin ions in the sample solder plating solution can be separately and independently determined using the various methods described hereinabove for "TIN ANALYSIS."

The concentration of lead can then be determined, by subtracting the tin concentration from the total metal concentration.

II. Direct Potentiometry

The lead concentration can also be directly determined, using a direct potentiometry method similar to that described for acid concentration determination, which comprises the steps of:

(a) measuring electropotential responses of one or more calibration solutions of known lead concentrations;

(b) determining the correlation between lead concentrations and electropotential responses of solutions, based on the calibration measurements;

measuring electropotential response(s) of the sample solder plating solution; and determining lead concentration in the sample solder plating solution, based on the electropotential response(s) measured in step (c) and the correlation determined in step (b).

The sample solder plating solution is preferably diluted before any measurement is conducted. For example, the sample solution may be diluted by adding the sample solution into deionized water or a concentrated electrolytic solution, so as to maintain the pH value of the sample solder solution above 3, where there is a much more stable potential response from the electrode.

One embodiment of the present invention uses the following steps for determining the lead concentration in a sample solder plating solution based on the direct potentiometry method described hereinabove:

A slope k was first determined, by measuring the electropotential responses of two successive standard additions of a lead concentrate (with known lead concentration therein) into deionized water using a lead ion selective electrode, according to the following equation:

$$k = \frac{E_{ii} - E_i}{\log 2}$$

Wherein $E_{ii}$ is the electropotential response measured after introduction of the second standard addition of the lead concentrate into the deionized water, and $E_i$ is the electropotential response measured after introduction of the first standard addition of the lead concentrate into the deionized water.

Slope k so determined is indicative of the correlation between lead concentration and electropotential response in a solution.

The electropotential of the sample solder plating solution can then be measured, using a lead ion selective electrode. It is preferred that the sample solder plating solution is diluted before the electropotential measurement. For example, the sample solution can be diluted 1/100, using deionized water.

Next, a standard addition of lead concentrate is added into the diluted sample plating solution, and the electropotential of the sample solder plating solution with the standard addition is measured by the lead ion selective electrode. Preferably, the amount of standard addition is controlled in such manner that the estimated lead concentration in the diluted sample solution is approximately doubled due to such standard addition.

The concentration of total lead in the sample solder plating solution can then be calculated, according to the following simplified equation:

$$C_l = \frac{V_A c_A}{V_s[\text{antilog}((E_2 - E_1)/k) - 1]}$$

Wherein $C_a$ is the concentration of lead ions in the sample solder plating solution, $V_A$ is the volume of the standard addition of lead concentrate added into the sample solder plating solution, $c_A$ is the concentration of lead in the standard addition, $V_S$ is the volume of the diluted sample soldering plating solution, $E_1$ and $E_2$ are the potential responses of the diluted sample plating solution measured before and after and the standard addition of the lead concentrate, respectively.

Initial experiments to determine lead concentration in the high lead sample solder plating solution (without tin) at pH levels below 3 showed unsatisfactory results, due to the electrode instability in such a highly acidic environment. It is therefore desirable to maintain the pH level above 3, where there is a much more stable potential response from the electrode, as quantified in Table 2 below:

TABLE 3

Electrode Response from High Lead Sample Solder Solution (without tin)

| | PH = 1.9 | | | PH > 3 (with acetate buffer) | | |
| --- | --- | --- | --- | --- | --- | --- |
| True Concentration (g/L) | Measured Concentration (g/L) | Potential Response (mV) | True Concentration (g/L) | Measured Concentration (g/L) | Potential Response (mV) | pH |
| 75 | 100 | 3 | 75 | 81 | 8 | 3.4 |
| | | | 65 | 68.70 | 8 | 3.4 |
| | | | 76 | 75 | 10 | 5 |
| | | | 65 | 70 | 10 | 5 |
| | | | 85 | 97 | 10 | 5 |

The effect of tin (4 g/L) on the lead concentration analysis was tested in a sample solder solution that contains high lead concentration (75 g/L). It was observed that the electrode potential responses took longer to stabilize, and the responses drifted after a period of time. The measured concentration of lead was 91.36 g/L, with a 21.8% error rate. Repeated measurements result in similarly high lead concentrations.

One way to reduce the error rate of the above-described lead concentration determination is to reduce the effect of the difference in activity coefficients between the sample solder plating solution and the standard addition, by diluting the sample solder plating solution in a concentrated solution of electrolyte. The dilution of sample solder plating solution is even more necessary when analyzing the eutectic sample solder plating solution, in which the concentration of tin is higher than that of lead.

III. Parallel Titration

The present invention proposes a parallel titration method for directly determining the lead concentration in a sample solder plating solution, which uses a primary titration solution comprising EDTA and a secondary titration solution comprising a strong base, preferably a metal hydroxide (such as NaOH or KOH).

EDTA (ethylenediaminetetraacetic acid) is a polyfunctional acid, which forms very strong complexes with the metal ions in the sample solder plating solution and releases protons. The released protons lead to detectable changes in the pH value of the sample plating solution and can be monitored by a pH probe. Therefore, the present invention employs a primary titration solution comprising EDTA for complexing with the metal ions in the sample solder plating solution, and a glass pH probe for monitoring the pH changes of the sample solution caused by EDTA addition.

Moreover, the present invention employs a secondary titration solution that comprises a strong base, such as NaOH or KOH, to neutralize the released protons after every EDTA addition, so as to compensate for the pH changes caused by the released protons and to ensure that the pH value of the sample plating solution is the same before every EDTA addition. In such manner, the glass pH probe accurately measures and records the pH drop caused by every EDTA addition, while each pH drop so measured and recorded has the same "starting point" and therefore can be compared with each other.

Specifically, the parallel titration method of the present invention starts with the step of conditioning a sample solder plating solution, by adjusting the pH value of such sample solder plating solution to a base value that is within a range of from about 4 to about 4.5. At this base value, the tin ions in the sample solder plating solution is already in the form of insoluble tin hydroxide ($Sn(OH)_2$), so that the sample solution appears slightly milky. The pH value of the sample solder plating solution can be adjusted by using a base solution comprising hydroxide ions ($OH^-$), such as NaOH or KOH.

Alternatively, the sample solution can first be subjected to a total acid concentration analysis using the incomplete titration method described hereinabove, during which the pH value of the sample solder plating solution is titrated to about 4, so that the sample solder plating solution can be used directly for lead concentration analysis according to the parallel titration method described hereinafter, without any sample conditioning or pH value adjusting step.

The protons released by the EDTA during the tin-EDTA complexing is immediately neutralized by the hydroxide ions from the tin hydroxide, so that no change of pH value is detected by the glass pH probe immersed in the sample solder plating solution, and that the pH value of the sample plating solution remains at the base value described hereinabove. The chemical reaction in this step is as follows:

$$Sn(OH)_2 + H_2EDTA \rightarrow SnEDTA + 2H_2O$$

On the other hand, at the base pH value of about 4–4.5, the lead ions are not in hydroxide form, unlike the tin ions, so the protons released by the EDTA during the lead-EDTA complexing are not neutralized, which cause an immediate pH drop in the sample solder plating solution that can be detected and recorded by the pH probe immersed therein. The chemical reaction in this step is as follows:

$$Pb^{2+} + H_2EDTA \rightarrow PbEDTA + 2H^+$$

In order to quantify the pH drop caused by each EDTA addition during the lead-EDTA complexing, a secondary titration solution comprising hydroxide ions is added into the sample solder plating solution after each EDTA addition, for neutralizing the protons released by the EDTA and for titrating the sample plating solution back to the above-mentioned base pH value. Such secondary titration solution may comprise one or more strong base compounds such as NaOH and/or KOH. By adding such secondary titration solution after each EDTA addition, the pH value of the sample plating solution is the same (i.e., equal to the base value) before next EDTA addition during the lead-EDTA complexing, so that the pH drop caused by each EDTA addition can be easily quantified and compared with each other. Another advantage of this titration of released protons is that the incremental additions of EDTA and titration of the so released protons ensures that the pH of the solution never decreases to low values that might cause precipitation of the EDTA complex (EDTA and complexes become less soluble as the pH decreases).

Successively decreasing amounts of EDTA are added into the sample solder plating solution for complexing with the lead ions therein, and the pH drop caused by each EDTA addition is measured by the pH probe and recorded. Moreover, the total amount of EDTA added and the total amount of the secondary titration solution added are monitored and recorded.

After all the lead ions in the sample solder plating solution have complexed with EDTA, further EDTA added therein does not complex with metal ions any longer, and no protons are released by the EDTA, so no pH drop is detected by the pH probe immersed in the sample solution. Therefore, detection of a constant pH value of the sample solder plating solution, despite continuous addition of EDTA, marks the ending of the lead-EDTA complexing.

Figure 10:
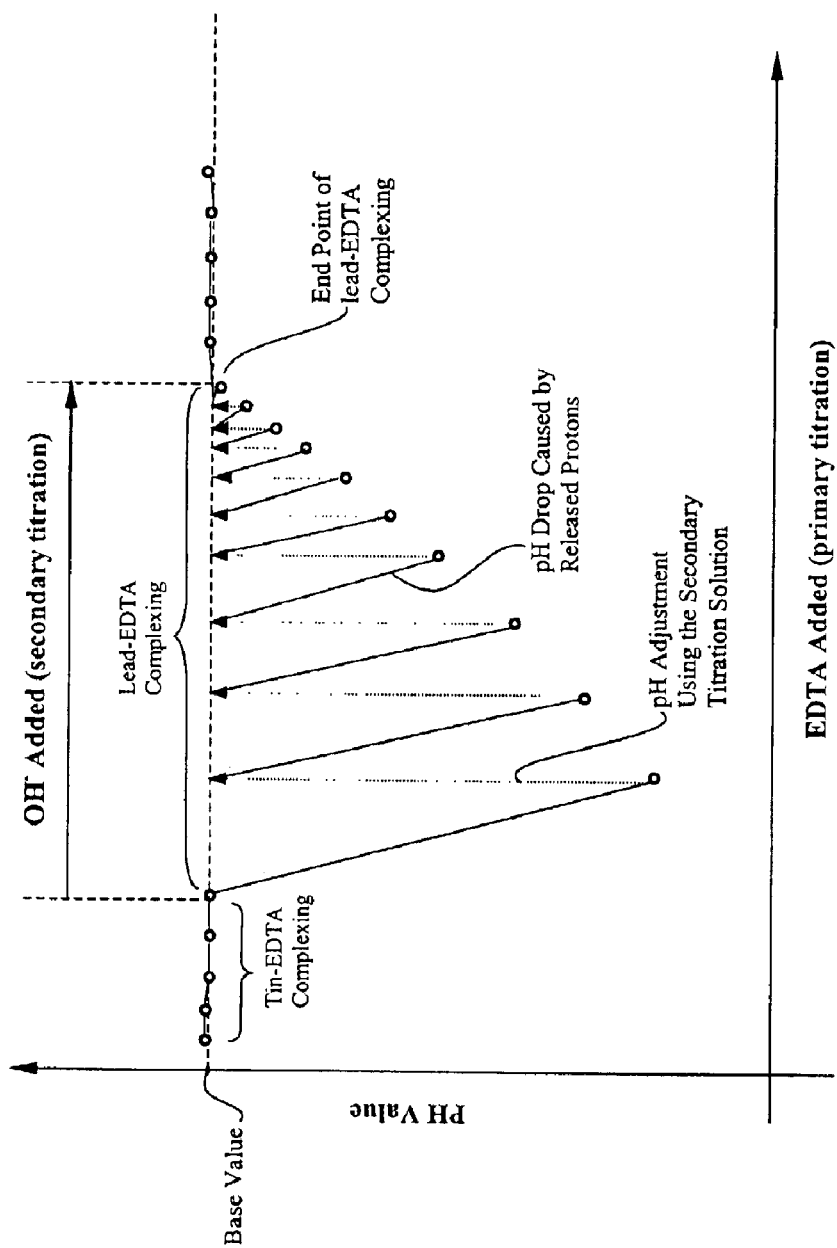
FIG. 10 shows the pH values of the sample solder plating solution during the parallel titration for lead and/or total metal analysis, in relation to the EDTA and the secondary titration solution containing OH⁻ added thereinto.

FIG. 10 illustrates the pH values of the sample solder plating solution during the parallel titration described hereinabove, in relation to the EDTA and the secondary titration solution containing $OH^-$ added thereinto. During the tin-EDTA complexing, the pH value of the sample solder plating solution remains the same at the base value, regardless of the continuous addition of EDTA. When the tin-EDTA complexing ends and the lead-EDTA complexing starts, each EDTA addition causes a pH drop in the sample solder plating solution, due to the protons released by the EDTA. Secondary titration solution comprising $OH^-$ is then added to the sample solder plating solution after each EDTA solution, so as to neutralize the released protons and adjust the pH value of the sample solution back to the base value. When the lead-EDTA complexing ends, further EDTA additions no longer cause pH drop in the sample solder plating solution, indicating that the end point of the lead-EDTA complexing is reached, and that no additional secondary titration solution is needed.

Therefore, by recording the total amount of OH⁻ added, one can directly and independently determine the lead concentration in the sample solder plating solution, without any correction.

Figure 11:
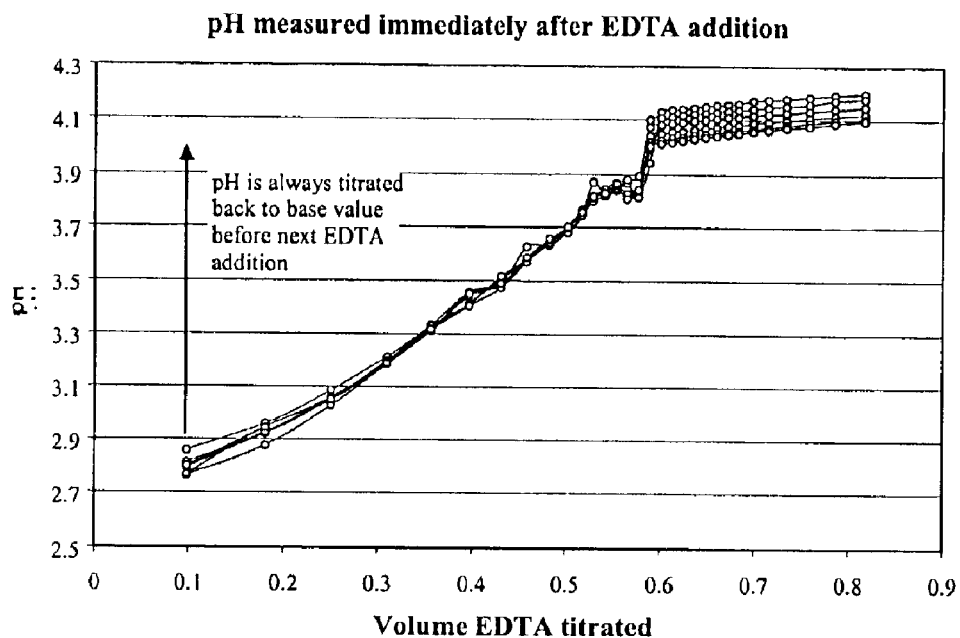
FIG. 11 shows multiple titration curves constructed for a sample solder plating solution according to the parallel titration method for lead and/or total metal analysis, plotting the pH value of the sample solder plating solution as a function of the volume of the EDTA addition.

FIG. 11 shows multiple titration curves constructed for a sample solder plating solution according to the parallel titration method described hereinabove, plotting the pH value of the sample solder plating solution as a function of the volume of the EDTA addition, starting from the point where the first pH drop in the sample solution is detected. As shown in FIG. 11, during the lead-EDTA complexing, each addition of EDTA causes a pH drop in the sample solder plating solution, while after the lead-EDTA complexing, EDTA addition no longer results in pH drop, as indicated by the flat "tails" of the titration curves.

Figure 12:
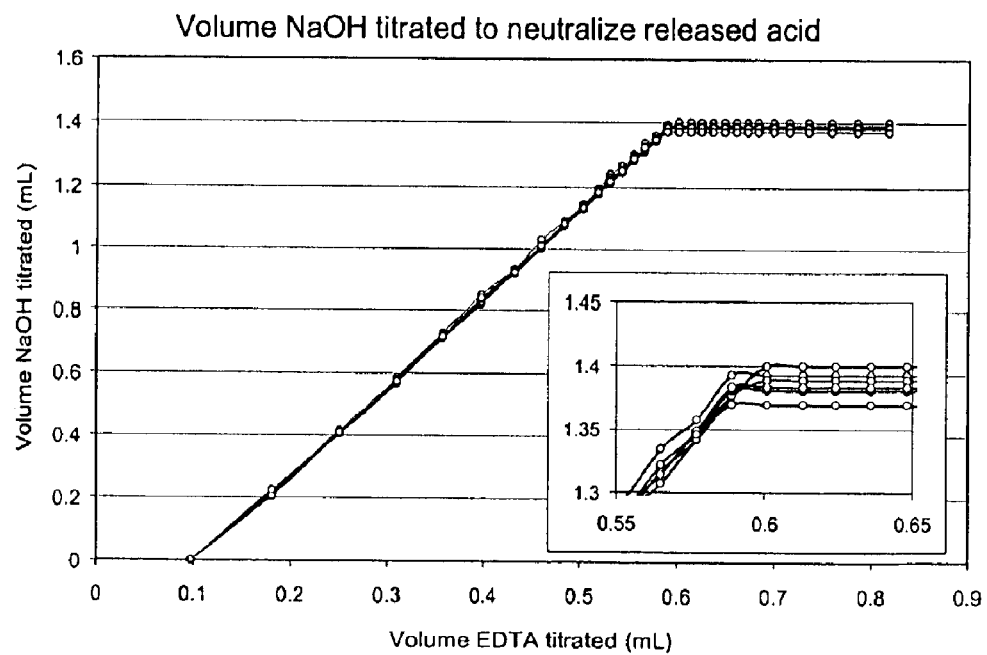
FIG. 12 shows multiple titration curves that plot the volume of NaOH (i.e., the secondary titration solution) added as a function of the EDTA added, during the parallel titration process of FIG. 11.

FIG. 12 shows multiple titration curves that plot the volume of NaOH (i.e., the secondary titration solution) added as a function of the EDTA added. The NaOH is added into the sample solder plating solution after each EDTA addition, for neutralizing the released protons and for adjusting the pH value of the sample solution back to the base value. The ratio of NaOH: EDTA is approximately 2:1 during the lead-EDTA complexing, as shown by FIG. 12. After the lead-EDTA complexing, no more NaOH solution is added, as indicated by the flat "tails" of the titration curves. The total volume of NaOH used during the parallel titration process can be used for direct calculation of the lead concentration in the sample solder plating solution, because NaOH is only used during the lead-EDTA complexing, and the amount of NaOH consumed is stoichiometric with respect to the lead concentration in the sample solution.

Polymeric Non-Ionic Surfactant Analysis

I. Potentiostatic Methods

The present invention in one embodiment employs potentiostatic methods for determining the concentration of polymeric non-ionic surfactant in solder plating solutions.

Cyclic voltammograms scan (CVS) at a scan rate of 100 mV/s were collected in eutectic solder plating solutions that contain polymeric non-ionic surfactant at concentrations varying from 0 to 26 mL/, at an electrode rotation speed of 1200 rpm L.

A diffusion-limited current plateau was observed when the electrode potential applied was between −0.5 and −0.6 V versus Ag/AgCl reference electrode. Such diffusion-limited current plateau was stable and reproducible, only slightly dependent on the electrode potential. Such diffusion-limited current plateau is likely caused by a potential-independent diffusion process, while metal cations penetrate through the adsorbed surface layer on the electrode.

At more negative electrode potentials, an unlimited increase in the plating current occurred, which was persistent in the anodic portion of the voltammetric scan. This unlimited current increase is likely caused by a transition from a "smooth" stage to a "dendritic" stage in metal growth on the electrode surface.

The inventors of the present invention have discovered that the time required for the transition from the diffusion-limited current plateau to the unlimited increase of the plating current depends on both the electrode potential applied on the electrodes and the organic polymeric non-ionic surfactant concentration in the sample solder plating solution. When the electrode potential applied is held constant, such transition time correlates with the polymeric non-ionic surfactant concentration in the sample solder plating solution, and it therefore can be used for polymeric non-ionic surfactant analysis.

On the other hand, the inventors have discovered that the analytical signals (such as the plating current or the stripping charge), as measured during the occurrence of the unlimited plating current increase, are strongly dependent on the concentration of polymeric non-ionic surfactant in the solder plating solution. In fact, when the polymeric non-ionic surfactant was titrated into an inorganic matrix of solder plating solution, sigmoidal dependency similar to that of conventional titration curves was observed.

Therefore, by monitoring the analytical signals during the occurrence of the unlimited increase in plating current, one can readily determine the concentration of polymeric non-ionic surfactant in the solder plating solution.

Both linear potential scan analysis and potential step plating-stripping analysis can be used to measure the analytical signal during such occurrence of the unlimited plating current increase.

During such measurement, the anodic limit of the potential region is preferably more negative than +0.1 V versus saturated calomel electrode (SCE) vs Ag/AgCl. Plating potential in a range of from about −0.60 to −0.70 V versus Ag/AgCl is generally adequate for measuring sample solder plating solutions with a polymeric non-ionic surfactant concentration of 0.5 to 2 mL/L.

Stripping charges rather than plating currents are preferably used herein as the analytical signal, since use of stripping charges results in reduction of noise, as well as reduction of interference caused by hydrogen evolution and oxygen reduction. More preferably, normalized stripping charge is used.

Each plating cycle is preferably conducted with a plating time of about 15 seconds, or a plating time of about 2–5 seconds. The stripping potential is preferably about −0.15 V versus Ag/AgCl. In order to avoid large anodic currents (100 mA), an even smaller stripping potential of about −0.25 V or −0.3 V vs. Ag/AgCl can be used.

For the purpose of optimizing the measurement results in the present invention, a series of optimization tests were conducted. For the linear potential scan analysis, the optimal parameters were found to be: cathodic limit −650±25 mV, scan rate 50–100 mV/s, and end point at 0.700 of the value in the eutectic VMS solution, with the sample being titrated into the eutectic VMS solution. For the potential step plating-stripping analysis, the optimal parameters were found to be: plating potential −625±25 mV, plating time 2–5 seconds, stripping potential −300 or −150 mV, and end point at 0.600 of the value in the eutectic VMS solution. The measurement temperature is preferably in a range of from about 30–45° C. Optimization tests for the present invention were conducted at 36.6° C., but better-defined inflection points can be obtained at higher temperatures, such as 40–45° C. When the temperature rises to about 50° C., the titration curves showed poorly defined transitions, and therefore it is desirable to control the measurement temperature at below 50° C.

II. Potentiometric Titration Method

The present invention in another embodiment employs a potentiometric titration method for determining the concentration of polymeric non-ionic surfactant in solder plating solutions.

The polymeric non-ionic surfactant used in solder plating solutions is generally a polyether or a polyalkalene glycol. Such non-ionic surfactant is capable of forming a weak complex with a large metal ion, such as barium, and therefore becomes cationic. Since the solder plating solutions contain a large amount of lead ions, which can form the cationic complex with the polymeric non-ionic surfactant therein, no additional metal ions need to be introduced in the present invention.

Therefore, potentiometric titration can be directly carried out in the present invention, by adding a sodium tetraphenylborate titrant solution into the sample solder plating solution, to form an insoluble reaction product with the lead/polymeric non-ionic surfactant complex in such sample solution. The end point of such potentiometric titration can be readily detected by a surfactant electrode. Commercially available surfactant electrodes suitable for the practice of the present invention can be obtained from Orion Research Inc., Boston, Mass.

Since the reaction between the lead/polymeric non-ionic surfactant complex and the sodium tetraphenylborate titrant is not stoichiometric, empirical titration factors must be established, by carrying out multiple potentiometric titration measurements on multiple standard solder plating solutions of known polymeric non-ionic surfactant concentrations, so as to correlate the volume of the sodium tetraphenylborate titrant used with the polymeric non-ionic surfactant concentration in the solder plating solutions.

The potentiometric titration method provides a quick and simple analytical process for the polymeric non-ionic surfactant analysis and generates reproducible and reliable measurement results.

Brightener Analysis

I. UV-Vis Spectrometry

The present invention in one embodiment employs UV-Vis spectrometry for determining concentration of the brightener in the solder plating solutions.

The first step for UV-Vis spectrometric analysis is to determine a suitable wavelength for the incident UV light, at which the absorption effectuated by the brightener is maximized. In order to find such suitable wavelength, the UV-Vis absorption spectra of various test solutions were obtained, which include (1) a solution containing methanesulfonic acid (MSA) and the brightener; (2) a solution containing MSA, the brightener, and tin ions; (3) a solution containing MSA, the brightener, tin ions, and lead ions; (4) a solution containing MSA, the brightener, tin ions, lead ions, and the antioxidant; and (5) a solution containing MSA, the brightener, tin ions, lead ions, the antioxidant, and the polymeric non-ionic surfactant.

Figure 13:
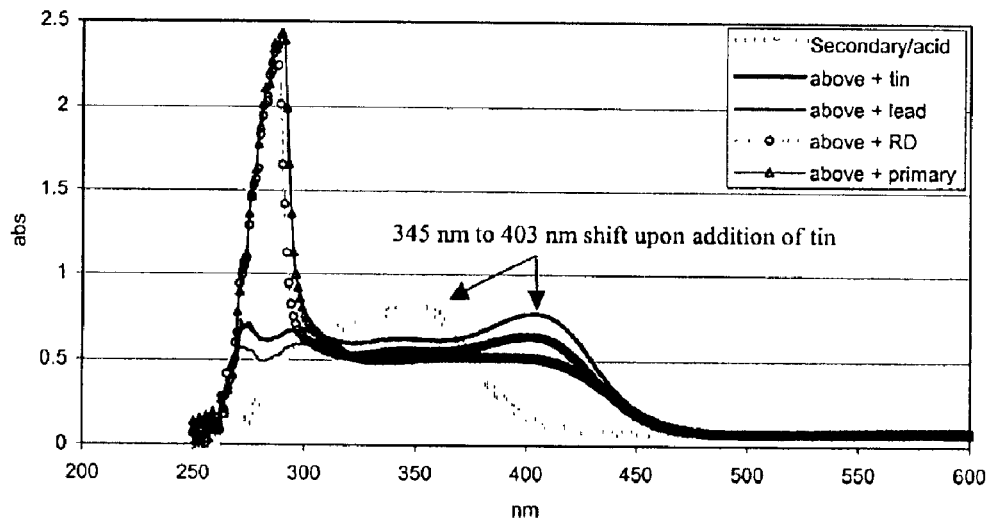
FIG. 13 shows UV-Vis absorption spectra obtained for various test solutions, including (1) a solution containing methanesulfonic acid (MSA) and the brightener; (2) a solution containing MSA, the brightener, and tin ions; (3) a solution containing MSA, the brightener, tin ions, and lead ions; (4) a solution containing MSA, the brightener, tin ions, lead ions, and the antioxidant; and (5) a solution containing MSA, the brightener, tin ions, lead ions, the antioxidant, and the polymeric non-ionic surfactant.

FIG. 13 shows the UV-Vis absorption spectra obtained for the above-mentioned test solutions. The solution containing only MSA and the brightener shows a single absorption peak at a wavelength of approximately 345 nm, while the solution containing tin ions in addition to MSA and the brightener shows a single absorption peak at a different wavelength of approximately 403 nm. Therefore, addition of tin ions causes the absorption peak to shift by approximately 60 nm, which may be contributed to formation of a tin/brightener complex. The addition of lead ions has little effect upon the position of the absorption peak.

The solution containing MSA, the brightener, tin and lead ions, and the antioxidant shows two absorption peaks, one at a wavelength of approximately 276 nm, and the other at a wavelength of approximately 403 nm. Similarly, the solution containing MSA, the brightener, tin and lead ion, the antioxidant, and the polymeric non-ionic surfactant shows two absorption peaks at 276 nm wavelength and 403 nm wavelength, respectively. The second absorption peak at 403 nm wavelength is contributed to the tin/brightener complex, while the first absorption peak at 276 nm wavelength is contributed to both the polymeric non-ionic surfactant and the antioxidant.

Therefore, the wavelength of approximately 403±10 nm, preferably 403 nm±5 nm, and more preferably 410 nm, is chosen for conducting the UV-Vis spectrometric analysis of the brightener concentration in solder plating solution.

The incident UV light is provided by an UV light source, preferably a super-bright white LED. A filter is arranged between the UV light source and an analytical chamber that contains the sample solder plating solution to be analyzed, and such filter permits only UV light having wavelength within the suitable range (i.e., approximately 403±10 nm, preferably 403 nm±5 nm, and more preferably 410 nm) to pass therethrough.

A UV detector is provided on the other side of the analytical chamber, opposite to the UV light source and the filter, for measuring the amount of UV light that passes through the analytical chamber, and determining the amount of UV light absorbed by the sample solder plating solution in such analytical chamber.

According to Beer's law, the absorbance A varies with the concentration c of a specific species in a solution, and a linear relationship between the absorbance A and the concentration c, as follows:

$$A = \epsilon \times b \times c$$

wherein $\epsilon$ is the molar absorbtivity of the species, and b is the path length of the sample (i.e., the path length of the cuvette in which the sample is contained).

However, Beer's law is only accurate for adequately diluted solutions. In highly concentrated solder plating solutions, fluctuations in the absorbance measured were observed, while in highly diluted solder plating solutions, no absorbance was observed, due to background interference from the eutectic solder solution and the small absorbtivity $\epsilon$ displayed by the brightener in such diluted plating solution.

Therefore, it is desirable to dilute the solder plating solution before the UV-Vis measurement, by using deionized water. The dilution ratio is preferably within 10–100 for a nominal eutectic solder plating solution (having a brightener concentration of 5 mL/L) or a high lead solder plating solution.

In one specific embodiment of the present invention, standard additions of the brightener of known concentration is successively added into a standard eutectic solder solution that contains only inorganic components, without any polymeric non-ionic surfactant or antioxidant therein. The absorbance at approximately 410 nm is then measured for each standard addition, so as to produce a linear calibration curve, by plotting brightener concentrations as a function of the absorbance measured.

The absorbance of the sample eutectic solder plating solution, which contains all the components including the organic additives (approximately 100 mL/L polymeric non-ionic surfactant, 5 mL/L brightener, and 10 mL/L antioxidant), can then be measured at similar wavelength, i.e., approximately 410 nm. By using the calibration curve previously constructed, the concentration of the brightener in the sample eutectic solder plating solution can be readily determined.

Figure 14:
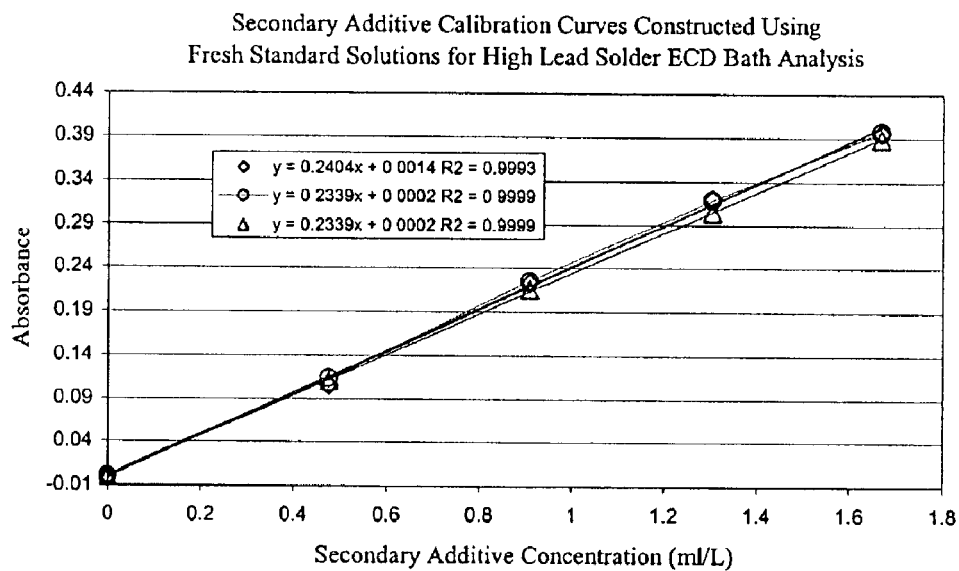
FIG. 14 shows three separate calibration curves constructed for the brightener analysis according to the UV-Vis spectrometric method, using fresh standard brightener solutions.

FIG. 14 shows three separate calibration curves constructed for the brightener analysis, which demonstrate good reproducibility of the UV-Vis spectrometric method described hereinabove. The linearity of these calibration curves is excellent, showing very little drift.

In an alternative embodiment of the present invention, an extrapolation method is used for conducting the UV-Vis spectrometric analysis and for determining the concentration of the brightener.

Specifically, such extrapolation method comprises the following steps:

First, the absorbance of the sample eutectic solder plating solution, which contains all the components including the organic additives (i.e., the polymeric non-ionic surfactant, brightener, and antioxidant), is measured at a wavelength of about 410 nm and recorded as $A_0$.

Standard additions of brightener of known concentration are then successively added to the sample solder plating solution. The absorbance of such sample solution after each standard addition of brightener is measured and successively recorded as $A_1, A_2, A_3 \ldots$. The brightener concentration of such sample solution after each standard addition are also calculated and successively recorded as $C_1, C_2, C_3, \ldots$, as shown in FIG. 15.

Figure 15:
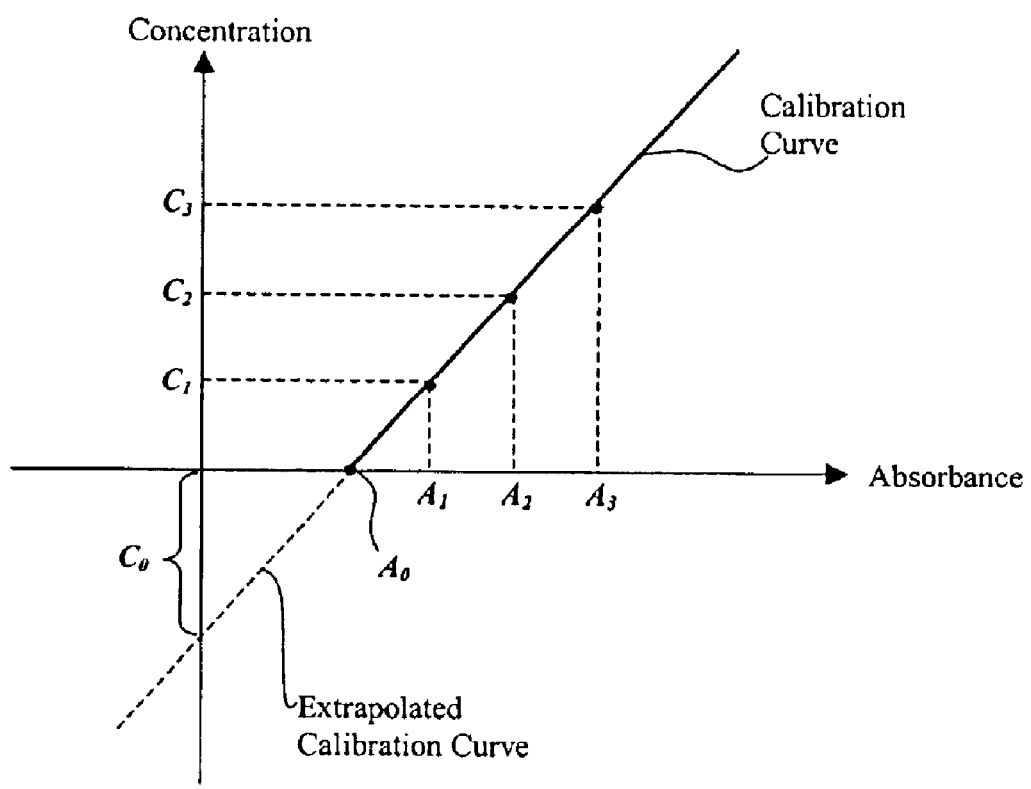
FIG. 15 shows a linear calibration curve, which plots increased brightener concentration caused by each standard addition of brightener, as a linear function of absorbance measured for a nominal solder plating solution after each standard addition of brightener therein.

A linear calibration curve can then be constructed, which plots the brightener concentrations $C_1, C_2, C_3 \ldots$ as a linear function of the absorbance $A_1, A_2, A_3, \ldots$, as shown in FIG. 15.

By extrapolating such linear calibration curve back to intercept with the y-axis (shown as the concentration axis), a y-intercept value is obtained. The absolute value of such y-intercept, shown as $C_0$ in FIG. 15, indicates the original brightener concentration in the sample solder plating solution before introduction of any standard addition.

The extrapolation method described herein above minimizes the difference between the sample solder plating solution and the calibration solutions. By directly adding standard additions of brightener into the sample solder plating solution, it eliminates potential measurement errors that may be caused by the presence of polymeric non-ionic surfactant and antioxidants in the sample solder plating solution and the absence of such polymeric non-ionic surfactant and antioxidants in the calibration solutions.

Figure 16:
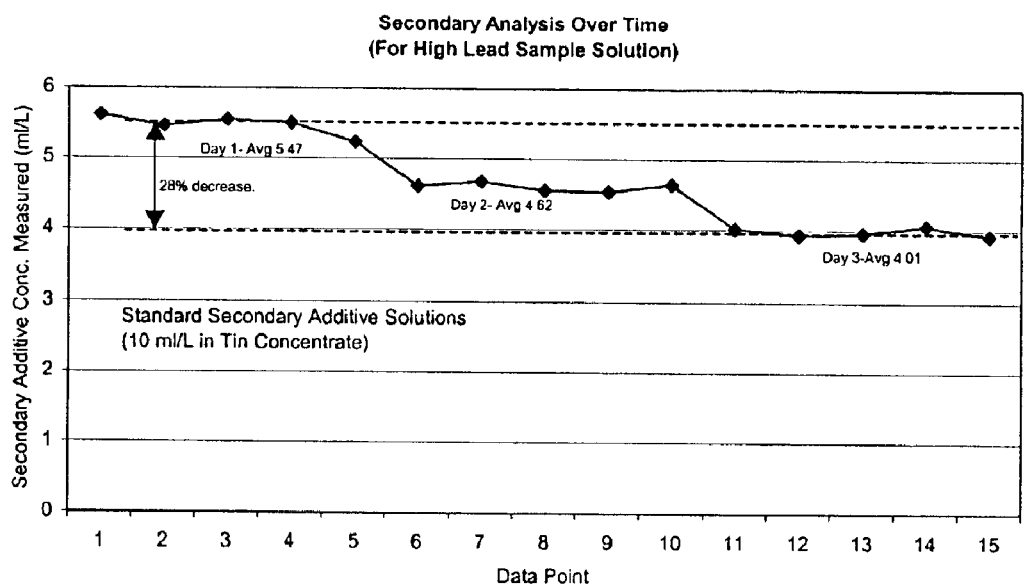
FIG. 16 shows the initial measurement result obtained using fresh standard brightener solutions, in comparison with measurement results subsequently obtained using the same brightener standard solutions, but after such standard solutions have sit for a certain period of time up to three days, according to the UV-Vis spectrometric method for brightener analysis.

The above-described analytical methods for determining brightener concentration are subject to errors caused by degradation of the standard brightener solutions. FIG. 16 shows the initial measurement result obtained using fresh standard brightener solutions, in comparison with measurement results subsequently obtained using the same standard solutions, but after such standard solutions have sit for a certain period of time up to three days. It is evident that subsequent measurement results slowly drifted away from the initial results when time passed.

It is believed that the degradation of the standard brightener solutions results in formation of particulates in the solder plating solution to be measured, which directly affects the absorbance of such solution and causes measurement errors.

Figure 17:
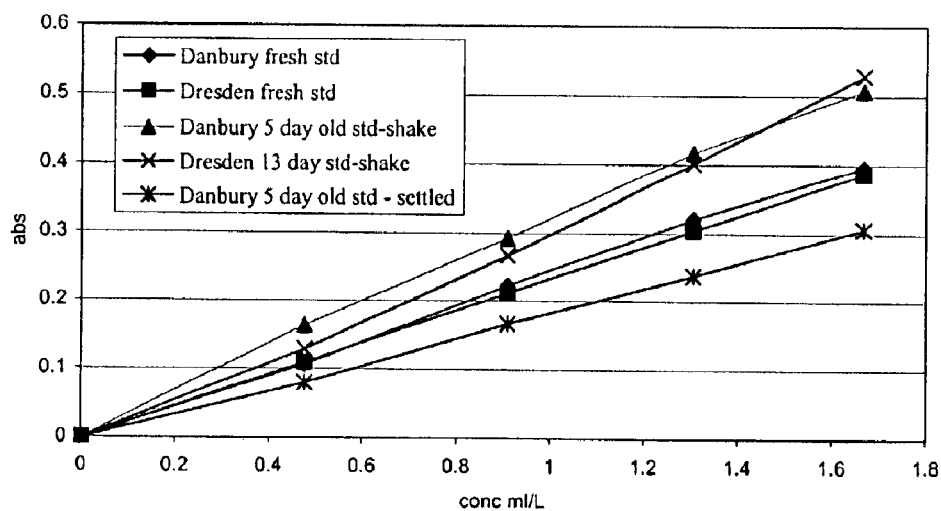
FIG. 17 shows various UV-Vis absorption calibration curves that were constructed by using standard brightener solutions of the same concentration but of different ages.

FIG. 17 shows various absorption calibration curves that were constructed by using standard brightener solutions of the same concentration but of different ages. Specifically, a calibration curve, which was constructed by using a fresh standard brightener solution from Advanced Technology Materials, Inc. ("ATMI") at Danbury, Conn. and identified as "Danbury fresh std," is compared to (1) a calibration curve constructed by using a shaken 5-day-old standard brightener solution provided by ATMI and identified as "Danbury 5 day old std-shake," and (2) a calibration curve constructed by using an unshaken (i.e., settled) 5-day-old standard brightener solution provided by ATMI and identified as "Danbury 5 day old std-settled." The absorbance of the "Danbury 5 day old std-settled" calibration curve is about 25% less than that of the "Danbury fresh std" calibration curve, while the absorbance of the "Danbury 5 day old std-shake" calibration curve is about 20% more than that of the "Danbury fresh std" curve.

Further, a calibration cure, as constructed by using a fresh standard brightener solution from AMD Saxony Manufacturing GmbH ("AMD") at Dresden, Saxony and identified as "Dresden fresh std," is compared to a calibration curve constructed by using a shaken 13-day-old standard brightener solution provided by AMD and identified as "Dresden 13 day std-shake." The absorbance of the "Dresden 13 day std-shake" calibration curve is about 20% more than that of the "Dresden fresh std" calibration curve.

Therefore, in order to prevent the loss of precision caused by the degradation of the standard brightener solutions, or the formation of particulates due to such degradation, it is preferred to use freshly made brightener solutions for standard additions. Alternatively, a filtering mechanism is preferably used for filtering out the particulates formed in the brightener solutions.

Antioxidant Analysis

The antioxidant used in solder plating solution is a catechol species, which serves as an antioxidant in eutectic solder plating solutions, in order to prevent oxidation of $Sn^{+2}$ to $Sn^{+4}$.

The present invention proposes two methods for measuring the antioxidant concentration in solder plating solutions, which include an oxidation-reduction potential method and a UV-Vis spectrometry, as discussed hereinafter.

I. Oxidation-Reduction Potential (ORP) Method

The antioxidant (i.e., catechol) usually undergoes oxidation-reduction reaction in the solution, according to the following equation:

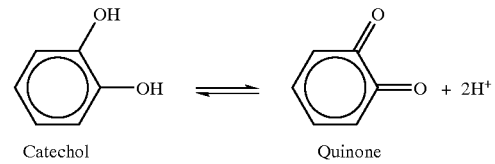

Catechol            Quinone

According to Le Chatelier's principle, the acidity of the catechol solution has an effect on the oxidation-reduction potential of the solution. Therefore, one embodiment of the present invention uses an oxidation-reduction potential electrode to monitor the oxidation-reduction potential response of the sample solder plating solution during acid titration.

Specifically, 1 or 2 ml of a sample solder plating solution, which had a pH of approximately −1, was added to 100 ml deionized water, so that the pH of the diluted sample solder plating solution was approximately 1. An oxidation-reduction potential (ORP) electrode was used to measure the oxidation-reduction potential of the diluted sample solder plating solution.

Subsequently, an acid titration solution (e.g., methanesulfonic acid) that was compatible with the solder plating solution (i.e., said acid does not form irreversible products with any component of the solder plating solution), was added into to the diluted sample plating solution, so as to change the acidity of the sample solder plating solution, by raising the pH value of said sample solder plating solution to a predetermined level.

The oxidation-reduction potential of the sample solder plating solution during such acid titration process was measured by the ORP electrode and used to construct an oxidation-reduction potential response curve, by plotting the oxidation-reduction potential as a function of the pH value of the sample solder plating solution. The slope k of the oxidation-reduction potential response curve was determined for the sample solder plating solution, based on the measurements described hereinabove.

Such slope k was then compared with slopes of oxidation-reduction potential response curves constructed for several calibration solder plating solutions of known antioxidant concentration, for the purpose of determining the antioxidant concentration in the sample solder plating solution.

Figure 18:
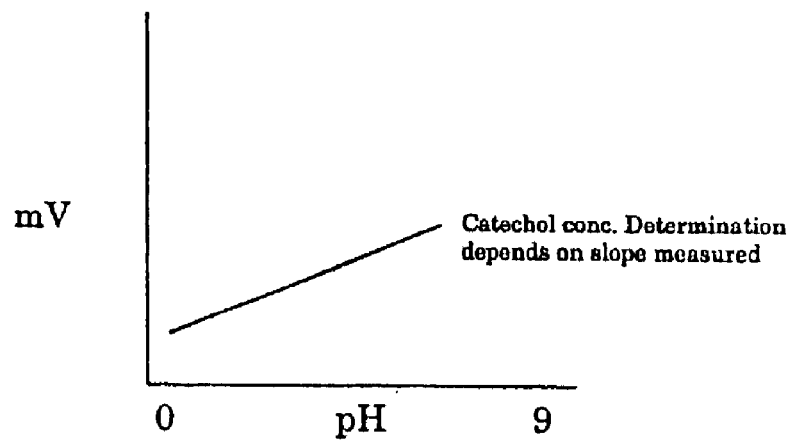
FIG. 18 is a graph plotting the oxidation-reduction potential of a sample solder plating solution as a function of the pH value of such sample solution, for antioxidant analysis.
Figure 19:
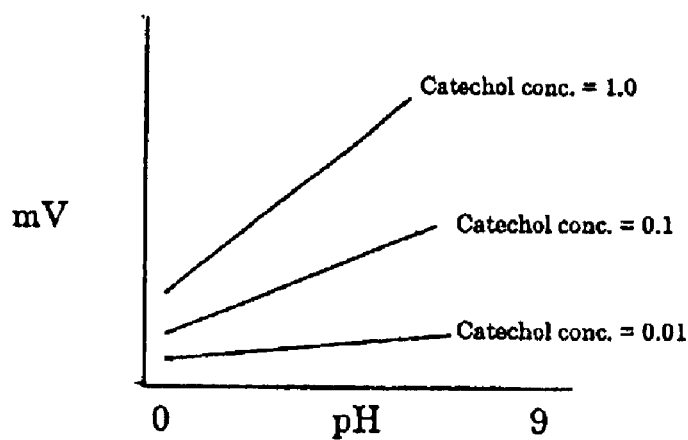
FIG. 19 shows three oxidation-reduction potential response curves, each of which plots the oxidation-reduction potential of a calibration solder plating solution of known antioxidant concentration, as a function of the pH value of such calibration solution, for antioxidant analysis.

FIG. 18 shows a graph that plots the reduction-oxidation potential response measured for a sample solder plating solution, as a linear function of the pH value of such sample solution. FIG. 19 shows a graph that contains three calibration curves showing the oxidation-reduction potential responses measured for three calibration solutions of known antioxidant concentration.

II. UV-Vis Spectrometric Methods

The present invention in another embodiment employs UV-Vis spectroscopy techniques for determining antioxidant concentration in solder plating solutions. The UV-Vis spectroscopy can be conducted either by detecting formation of an antioxidant-derivative, or by direct detection of the antioxidant molecule in the solder plating solution.

I. RD-Ferric Complex

One specific embodiment of the present invention involves using ferric chloride to form a blue complex with the antioxidant, which has a maximum absorbance around 750 nm and is detectable by UV-Vis spectrometry. Such antioxidant-ferric complex decomposes in approximately 5–20 minutes in water, but it is stable in methanol solution. Addition of pyridine to the methanol solution decreases the transient period of color development, increases the maximal extinction coefficient by about 3–5 times, and blue-shift the absorption maximum to 600 nm.

Therefore, a $FeCl_3$/Pyridine/Methanol solution is employed by the present invention for complexing with the antioxidant in the solder plating solution.

For example, 0–450 $\mu$m standard antioxidants can be added into a methanol solution comprising 12.5 mM pyridine and 7.5 mM ferric chloride. Experimental results show that such standard antioxidants produced a linear calibration curve with stable absorbance reading within two minutes after the mixing of the antioxidants with the $FeCl_3$/Pyridine/Methanol solution.

Preferably, the UV-Vis absorbance reading is conducted using antioxidant as extracted from the aqueous solder plating solution, so as to eliminate the deleterious impact of the solution matrix. More preferably, ethylacetate is used for extracting the antioxidant from the solder plating solution.

Figure 20:
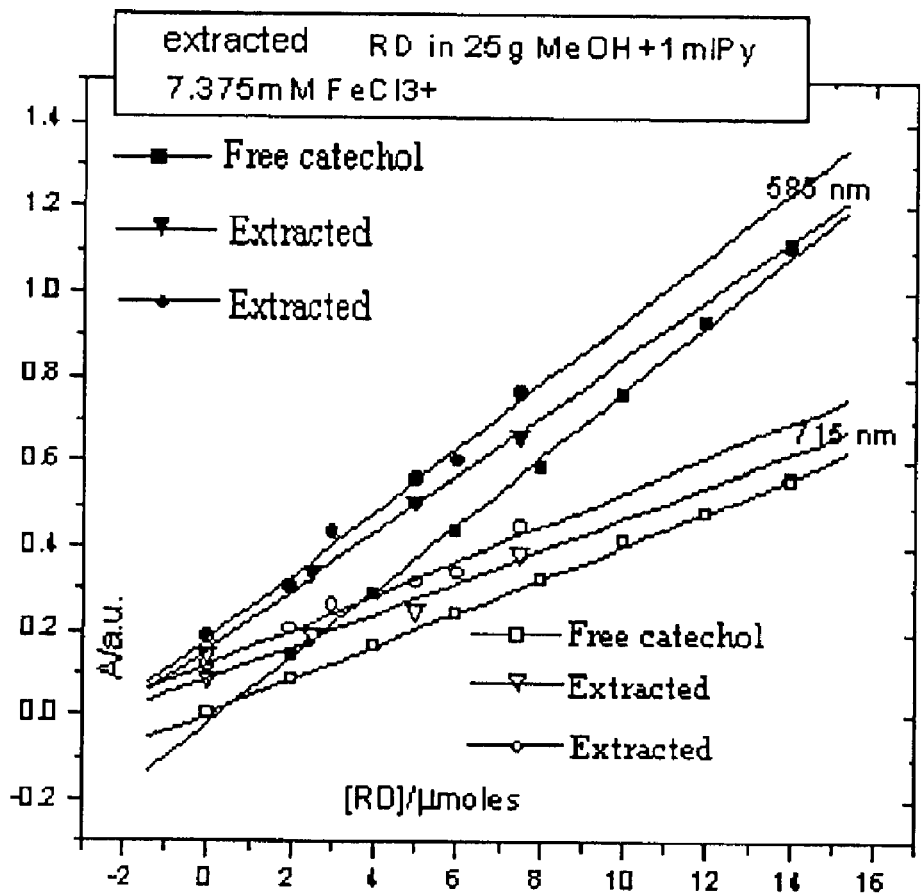
FIG. 20 shows various UV-Vis absorption calibration curves measured for antioxidant-ferric complex, using either free antioxidant solutions or antioxidant extracted from a sample solder plating solution.

FIG. 20 shows two calibration curves marked by squares, which were obtained by adding a freshly made 0.1 M aqueous solution of antioxidant to a 25 g (35 ml) $FeCl_3$/Pyridine/Methanol solution that contained 12.5 mM pyridine and 7.5 mM $FeCl_3$ in methanol. The calibration curve marked by the solid squares was measured at a wavelength of about 585 nm, and the calibration curve marked by the open squares was measured at a wavelength of about 715 nm. Both curves show linear absorption responses.

FIG. 20 also shows two calibration curves marked by circles (either open or solid), which were obtained by extracting the antioxidant from a fresh eutectic samples prepared with neat antioxidant solution, by using ethylacetate. Specifically, 10 ml of each sample were extracted with 2 ml of ethylacetate, and 0.1 ml of the extract was injected into 25 g (35 ml) $FeCl_3$/Pyridine/Methanol solution that contained 12.5 mM pyridine and 7.5 mM $FeCl_3$ in methanol. The calibration curve marked by solid circles was measured at a wavelength of about 585 nm, and the calibration curve marked by open circles was measured at a wavelength of about 715 nm. Both calibration curves marked by circles (either open or solid) show linear absorption responses. Moreover, the slopes of such calibration curves marked by circles, as obtained using extracted antioxidant, are equal to 95% of the slopes of the calibration curves marked by squares, as obtained using fresh antioxidant solution, which indicates that the extraction of the antioxidant is quantitative.

FIG. 20 further contains two calibration curves marked by triangles, which were obtained by using ethylacetate to extract the antioxidant from a Solderon® SC antioxidant concentration commercialized by Shipley Ronal at Marlborough, Mass. The abscissas of the data points were calculated under the assumption that the Solderon® SC antioxidant concentrate has a catechol concentration of about 1M.

In a preferred embodiment of the present application, the UV-Vis spectroscopic analysis of a nominal eutectic sample as described hereinabove can be performed in an automated analyzer, while extraction and analysis of the antioxidant can be carried out in a photometric cell of such automated analyzer.

Generally, about 10 ml of the sample solder plating solution is used for a UV-Vis spectroscopic analysis in such automated analyzer, and the total volume of the sample solder plating solution plus the ethylacetate solution is about 15 ml. After the ethylacetate extraction, approximately 0.3 ml of the antioxidant extract is injected into the photometric cell for automatic UV-Vis spectroscopic analysis. The photometric cell is preferably filled with about 16 ml of the $FeCl_3$/Pyridine/Methanol solution for measuring the reference light intensity of the solution (i.e., the reference measurement). Approximately 6 ml of the $FeCl_3$/Pyridine/Methanol solution is used to transfer the 0.3 ml antioxidant extract into the photometric cell. The antioxidant/$FeCl_3$/Pyridine/Methanol mixture solution is stirred for about 45–50 seconds and allowed to settle for about 45–50 seconds, and the photometric reading of such mixture solution then proceeds.

The following Table 4 show the results of UV-Vis spectroscopic analyses conducted with various rinsing procedures, which included (1) no rinse, (2) rinse with 10 ml of the $FeCl_3$/Pyridine/Methanol solution, and (3) rinse with 20 ml of the $FeCl_3$/Pyridine/Methanol solution.

TABLE 4

Light Intensity and Absorbance Measurements using Different Rinsing Methods

| Method # | Reference Light Intensity | Sample Intensity 90 s after Injection | Sample Absorbance at 600 nm and 90 s after Injection | Sample Intensity 180 s after Injection | Sample Absorbance at 600 nm and 180 s after Injection |
|---|---|---|---|---|---|
| #1 | 5.520 | 1.830 | 0.479 | 1.110 | 0.697 |
| #2 | 4.43 | 1.462 | 0.481 | 1.105 | 0.603 |
|  | 4.13 | 1.308 | 0.499 | 0.95 | 0.638 |
| #3 | 4.39 | 1.165 | 0.576 | 0.815 | 0.731 |
|  | 4.38 | 1.366 | 0.506 | 0.965 | 0.657 |
| Mean |  |  | 0.508 |  | 0.665 |
| RSD |  |  | 7.8% |  | 7.5% |

Method #1 No rinse
Method #2 Rinse the photometric cell with 10 ml $FeCl_3$/Pyridine/Methanol before the reference solution is introduced into the cell
Method #3 Rinse the photometric cell with 20 ml $FeCl_3$/Pyridine/Methanol before the reference solution is introduced into the cell The measurement results show that the sample absorbance measured with or without the rinsing step is sufficiently consistent, with only 7.8% relative standard deviation (RSD).

II. Antioxidant-Molybdenum Complex

An alternative embodiment of the present invention involves use of molybdate ions to form a yellow-orange colored antioxidant-molybdenum complex with the antioxidant, which can be readily measured via UV-Vis spectroscopy.

Figure 21:
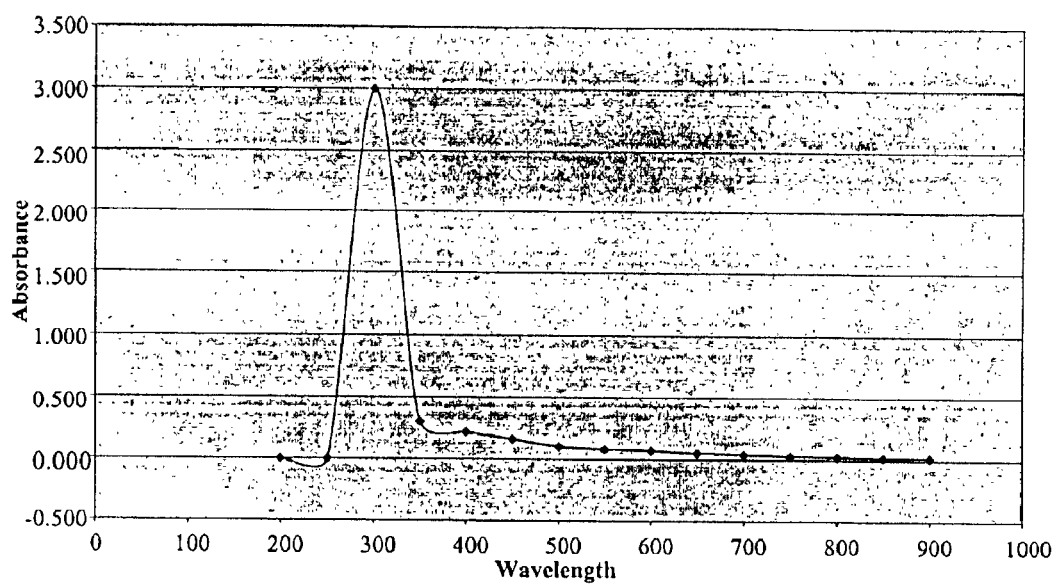
FIG. 21 shows the UV-Vis absorption spectrum of the antioxidant-molybdenum complex, formed by adding neat antioxidant into a complexing solution containing molybdenum dichloride dioxide, ammonium acetate, and EDTA.

The wavelength at which the antioxidant-molybdenum complex shows maximum absorbance was first determined using a complexing solution containing molybdenum dichloride dioxide, ammonium acetate, and EDTA. Neat antioxidant was added into such complexing solution, and the UV-Vis spectrum of the solution was measured, as shown in FIG. 21. The antioxidant-molybdenum complex shows maximum absorbance at a wavelength in a range of from about 280 nm to about 320 nm, and approximately 300 nm.

Figure 22:
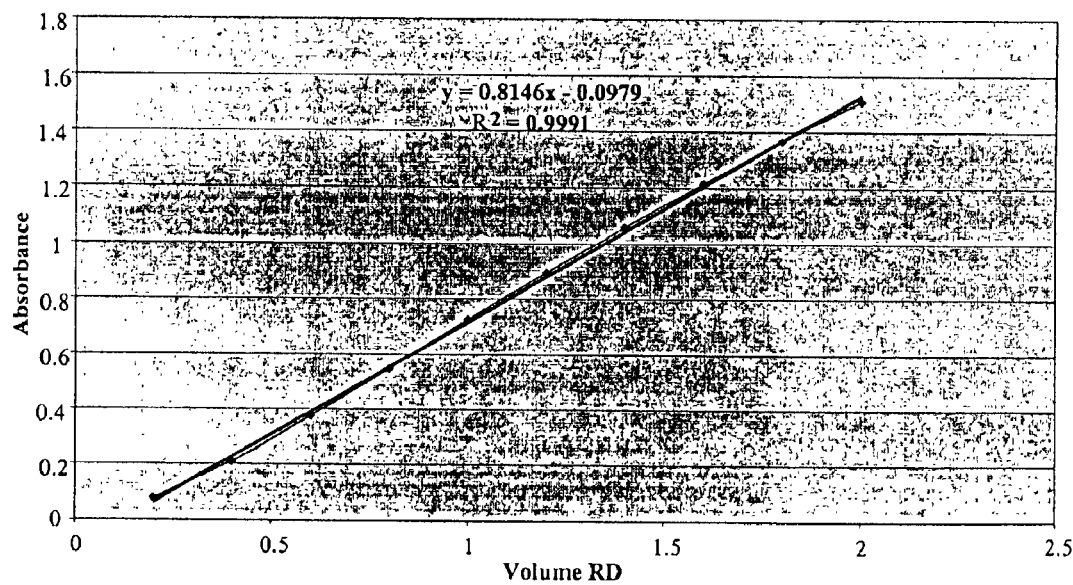
FIG. 22 shows the absorbance response measured for the $MoO_2Cl_2/NH_4C_2H_3O_2/EDTA$ complexing solution, as a function of the volume of neat antioxidant added into such complexing solution, for antioxidant analysis.

FIG. 22 shows the absorbance response measured for the $MoO_2Cl_2/NH_4C_2H_3O_2$/EDTA solution, as a function of the volume of neat antioxidant added into such solution. The absorbance response of the solution shows a linear relationship with the antioxidant concentration in the solution (i.e., volume of the antioxidant added into such solution), in compliance with Beer's law.

A complexing solution comprising 0.005M molybdenum dichloride dioxide, 1.5M ammonium acetate, and 0.1M EDTA can be used for forming the antioxidant-molybdenum complex, and the measurement results using such complexing solution demonstrated good reproducibility.

However, at high concentrations of molybdenum, a significant drift in the absorption measurements occurs, which reduces the accuracy of the UV-Vis spectrometric analysis. Such drift can be reduced by diluting the $MoO_2Cl_2$/$NH_4C_2H_3O_2$/EDTA solution by 4 or 5 times, using water and 2M ethanolamine solution. Experiments showed that such dilution can effectively reduce the drift in the absorption measurements to about 0.02 absorbance unit (AU) over a five minute period.

Figure 23:
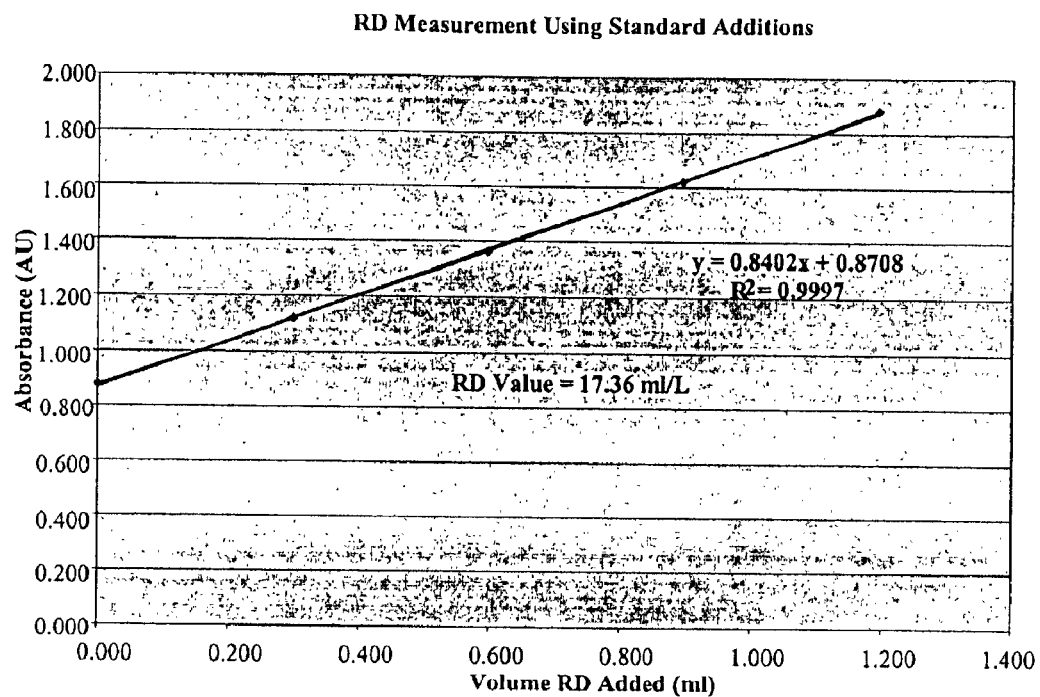
FIG. 23 shows a calibration curve, constructed to quantitate the relationship between the antioxidant concentration and the absorbance measured.

As a specific example, UV-Vis spectroscopic analysis of antioxidant concentration in a high lead solder plating solution, which comprises Sn, Pb, MSA, and antioxidant at a concentration of about 10 ml/L, was performed using 15 ml of the $MoO_2Cl_2/NH_4C_2H_3O_2$/EDTA solution as described hereinabove and 1.5 ml of the sample high lead solder plating solution. A calibration curve as shown in FIG. 23 was constructed to quantitate the relationship between the antioxidant concentration and the absorbance measured, using 0.5 ml antioxidant diluted in water with an additional 0.25 ml of neat ethanolamine added therein.

The present method for determining the antioxidant concentration in a sample solder plating solution overcomes the background interference from tin, lead, and brightener in such sample solution, and allows accurate determination of antioxidant concentration.

III. Direct UV-Vis Spectroscopic Measurement of Antioxidant

Direct detection of the antioxidant by UV-Vis spectrometric techniques at 276±20 nm may also be used for determining the concentration of antioxidant in a sample solder plating solution. UV-Vis spectrometric detection at such a short wavelength requires that the UV optics, the photometer board, and the UV detection devices be specifically designed for generating, transmitting, and sensing such short-wavelength UV light.

First, a small, inexpensive, long lived UV light source is provided for generating UV lights having wavelength of a broad spectrum, preferably from about 200 nm to about 2500 nm, and more preferably from 160 nm to about 5000 nm. Preferably, such UV light source has a low power consumption, i.e., it requires power of not more than 5 watts, more preferably not more than 2 watts, and it draws a peak current of not more than 2 amp, more preferably not more than 1 amp, which can be easily supplied by an onboard transformer. It is also preferred that such UV light source has a high emission intensity of at least 30 mJ/pulse, more preferably at least 40 mJ/pulse, and a high emission frequency of at least 25 Hz, more preferably at least 50 Hz. The size of such UV light source is preferably small, i.e., having a cross-sectional area of not more than 2 $dm^2$, more preferably, not more than 1 $dm^2$, and most preferably not more than 0.5 $dm^2$. The useful life of such UV light source is preferably at least $10^7$ pulses, and more preferably at least $10^8$ pulses. The warm-up time for such UV light source is preferably short, i.e., not more than 5 seconds, and more preferably not more than 1 second, and most preferably not more than 0.5 second. One particularly preferred UV light source suitable for practice of the present invention is the RSL 3100 series Xenon miniature flashlamp manufactured by PerkinElmer, Inc. at Wellesley, Mass. Other suitable UV light sources having operational characteristics as described hereinabove can also be used for practicing the present invention.

Secondly, optical filters that selectively transmit UV light of a wavelength in the vicinity of 276 nm (i.e., 276±20 nm), and block UV light of other wavelength are employed for providing a single beam of UV light having 276±20 nm wavelength. One group of optical filters particularly suitable for practicing the present invention are the narrow band interference filters manufactured by MK Photonics, Inc. at Albuquerque, N. Mex. Such narrow band interference filters from MK Photonics selectively transmit UV light having wavelength centered at 276 nm, with a full-width half-maximum (FWHM) of ±6 nm and a minimum peak transmission of 20%. Another group of optical filters that can be used for practicing the present invention are the broad band filters manufactured by Acton Research Corporation at Acton, Mass. Such broad band filters from Acton Research Corporation selectively transmit UV light having wavelength centered at 276 nm, with a FWHM of ±40 nm and a minimum peak transmission of 50%. Note that the selection of optical filters depends on the maximum absorption wavelength of the target species (which is 276 nm for the antioxidant, but can be above or belong such value for other target species), and the disclosure herein is only illustrative, while it does not intend to limit the broad scope of the present application in any manner. In other words, other types of optical filters provided by other manufacturers can be readily used for practicing the present application, consistent with the disclosure herein.

Figure 24:
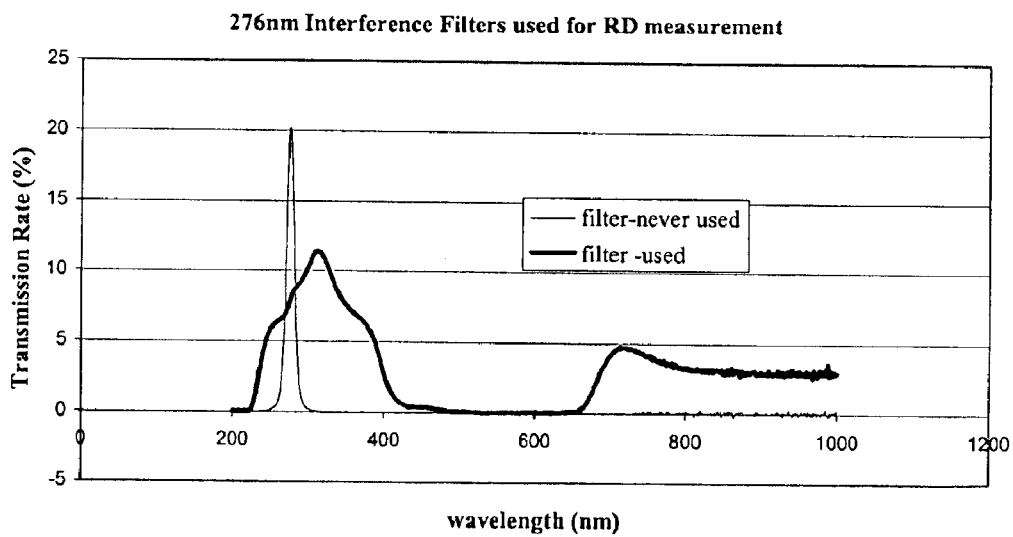
FIG. 24 plots the UV light transmission rate of an optical filter that has never been used as a function of the wavelength of the UV light transmitted by such filter, in comparison with the transmission rate and transmission wavelength of an optical filter that has been used for 3 months.

The optical filters used in the present invention are vulnerable to degradation, which significantly changes the optical characteristics and performance of such filters over time. For example, FIG. 24 shows a graph that plots the transmission rate of a filter that has never been used as a function of the wavelength of UV light transmitted by such filter, in comparison with the transmission rate and transmission wavelength of a filter that has been used for 3 months, indicating that the degradation of the optical filters leads to significant changes in the wavelength of the UV light transmitted by such filter and the transmission rate. Therefore, a periodic maintenance of at least once a month with respect to the optical filter is preferred.

Thirdly, the transmission of the filtered UV light to the sample solution to be analyzed and then to the detection device must be conducted using optical materials that are transparent to UV light, especially to UV light with wavelength of about 276 nm. Fiber optics is particularly preferred in the present invention, which can be incorporated into special adapters for adapting the UV light source to the optical cell. Low-hydroxl fibers are more preferred, and three different sizes of the fibers can be used to attenuate or increase light intensity, including 400 micron, 600 micron, and 1000 micron. SMA 905 multimode connector suitable for single fiber connections is most preferred for forming such adapters. Moreover, optically clear fluorinated ethylenepropylene (FEP) tape having a thickness of about 0.011 inch with adhesive backing can be used on the UV optics, which will provide longevity for the expensive UV optics and reduce the periodic maintenance frequency of such UV optics.

Figure 25:
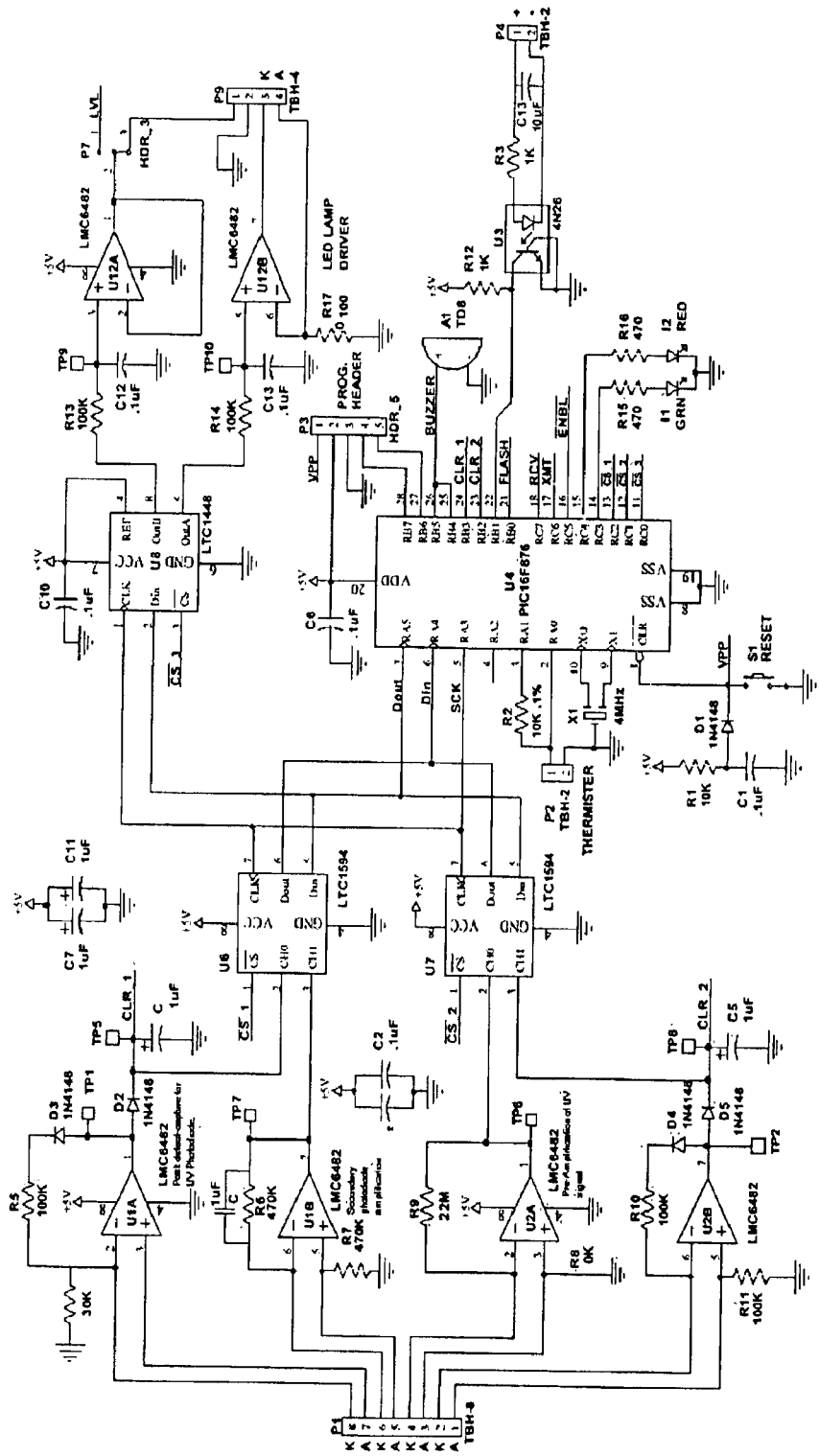
FIGS. 25 and 26 show a photometer board specifically designed for the UV-Vis spectroscopic measurements at short wavelength of about 276 nm.
Figure 26:
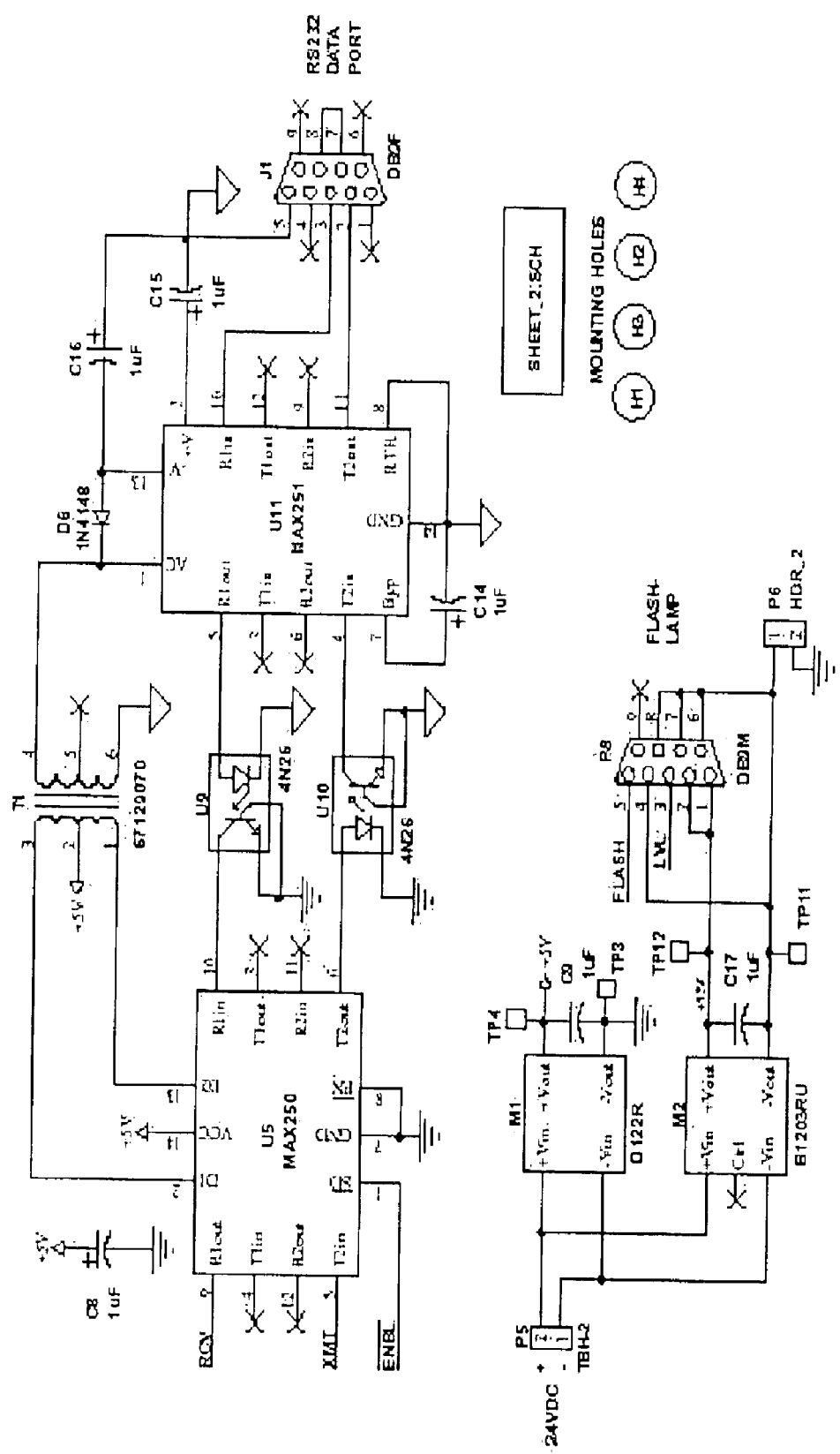

FIGS. 25 and 26 show new photometer board specifically designed for the UV-Vis spectroscopic measurements at short wavelength of about 276 nm, which allows dispersive measurement of the UV light emitted by pulsed or continuous UV light sources.

Note that such photometer board is hereby used for measuring the UV-Vis absorption spectrum of the antioxidant, which has a maximum absorption wavelength at 276 nm. However, such photometer board can also be used to measure other the UV-Vis absorption spectrum of other chemical species of different maximum absorption wavelength in the solder plating solution, by changing the optical filters used on the UV optics. For example, such photometer board can also be used for UV-Vis spectroscopic analysis of the brightener, using an optical filter for selectively transmit UV light having wavelength centered at about 403 nm (which is the maximum absorption wavelength for the tin/brightener complex). Therefore, the photometer board of the present invention can be arranged and configured to measure UV-Vis absorption spectrum of multiple components in a sample solder plating solution, by simple changing the optical filters used.

Such new photometer board houses the equivalents of two full spectrometers with reference features in addition to a temperature-sensing component. Further features of such photometer board include:

2 signal and 1 reference inputs on the board with Test Points (TP).

Dual LED control via constant current mode (P2) or one LED and one flash lamp (DB9M connector).

Ability to provide enough power for a UV flash lamp (12 V, 1 A).

An optically isolated 12V or 24V (resistor is changed to 2K, ½ watt) DC trigger can be accepted.

The 24 volt input is regulated down to an isolated 12V (M1) and 5V (M2) on the board.

Peak capture diodes (D2 & D3) on the signal inputs can capture microsecond transient signals.

optical fibers allowing flexibility in the light sources used.

The photometer board is a printed circuit board that contains specific electronics thereon. In addition to its analog-to-digital (ADC) and digital-to-analog (DAC) capabilities, it contains a PIC microprocessor that controls the sensor operations. The PIC is programmed by a PC, on which the source code for the sensor software is stored and compiled. Because the PIC is an EEPROM, it can be programmed by a personal computer (PC), shut off, and retain the stored information. Besides controlling all aspects of sensor operation, the PIC can be programmed directly from the PC and communicates serially via RS-232 protocol with a PC.

Through the RS-232 communications between the PIC microprocessor and a PC, the PC preferably provides a user interface for the photometer board. Furthermore, an interface program stored in the PC allows the user to save data from the sensors, set alarm and operational values in the sensor, and create a real-time, continuously updating graph of the sensor data.

The following Table 5 lists test points on the photometer board shown in FIGS. 25 and 26, corresponding to the devices used the their respective functions.

TABLE 5

| Testpoint/Pin | Device | Function |
| --- | --- | --- |
| TP1 | U1A | peak detect for antioxidant |
| TP2 | U2B | reserved for reference |
| TP3 | M1 | ground |
| TP4 | M1 | 5 V |
| TP5 | U1A | antioxidant signal on capacitor |
| TP6 | U2A | reserved for reference |
| TP7 | U1B | brightener signal |
| TP8 | U2B | peak detect for reference |
| TP9 | U12A | D/A output for UV/V is voltage signal. |
| TP10 | U12B | D/A output for controlling LED. |
| TP11 | M2 | Ground. |
| TP12 | M2 | 12 V DC for flashlamp. |
| 1 | U6 | Chip select for inputting brightener or antioxidant signal to D/A chip. |
| 1 | U7 | Chip select for inputting reference to D/A chip. |
| 3 | U6 | Clock for ensuring PIC is getting digital data from A/D chip U6. |
| 3 | U7 | Clock for ensuring PIC is getting digital data from A/D chip U7. |

The peak-detect-capture technique used with operational amplifier (see UIA of FIG. 25) allows measurement of a fast signal, through the following steps:

The Xenon flash lamp fires UV light, causing the hybrid photodiode to respond with a photo-generated current subsequently magnified by the on-board operational amplifier into a voltage pulse.

The voltage pulse travels down to the photometer board where it enters the operational amplifier non-inverting terminal on line A7 on connector P1.

The operational amplifier inverting terminal matches the non-inverting terminal and creates a pulse in the feed back circuit comprising a resistor R5 and two diodes D2 and D3.

The gain in the feed back circuit is 100K/30K while the diode allows charge to pass in one direction only to charge up the 0.1 microfarad capacitor at TP5, while preventing the capacitor from being discharged. The second diode compensates for the voltage drop over the first diode (0.7V), so that signals of less than the diode's 0.7V turn on voltage can be measured.

The charge is stored on the capacitor for 11 microseconds, and then the 12 bit Linear Technology LTC 1298 A to D chip (manufacture by Linear Technology Corporate at Milpitas, Calif.) converts the voltage into bits.

Roughly 75 microseconds later the capacitor is discharged and made ready to accept the next pulse.

The timing for this sequence of events is displayed in FIGS. 25–29 below. Note that it is possible to store more than 1 pulse on the capacitor at a time, and that the RS-232 communications on the board are disabled while the A/D and D/A converters are working to prevent device timing issues.

Figure 27:
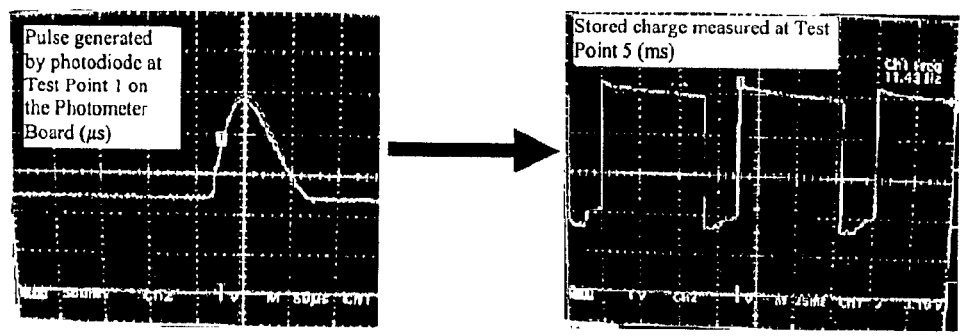
FIGS. 27–31 show the signals detected during various steps of the UV-light detecting process, including the firing of the UV flash lamp, the charging of a capacitor by a photodiode, the converting or translating of the stored charge into a digital signal, and the outputting of the digital signal to a personal computer.

FIG. 27 shows the pulse generated by the photodiode (for example, a SiC photodiode) in response to the flash of UV light generated by the flashlamp. Such pulse is converted into charge stored on a capacitor, which can be read by a A/D device. The left-hand picture depicts a pulse from the photodiode after it has been magnified by the operational amplifier as viewed from an oscilloscope trace at Test Point 1 (TP1) on FIG. 25. The right-hand picture depicts three repeated pulses from the photodiode, each pulse leading to stored charge on the capacitor as measured at Test Point 5 (TP5) on FIG. 25. Note that the timescales for the left-hand and right-hand pictures are different: the photodiode pulse is measured by microseconds ($\mu s$), which is approximately 100 $\mu s$, while the stored charge is measured by milliseconds (ms), which is approximately 75–80 ms.

Figure 28:
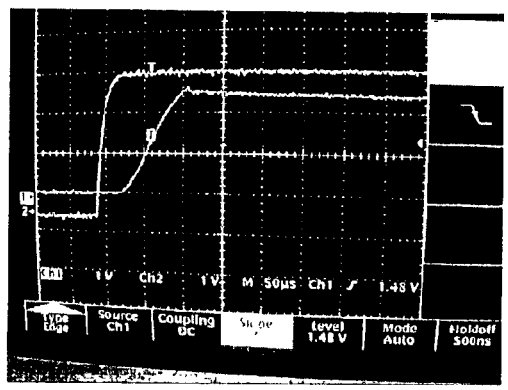

FIG. 28 shows the start of the signal process, where a 3.6V transistor-transistor logic (TTL) signal from the PIC microcontroller causes the flash lamp to fire a UV light pulse, and the end of the signal process, where a smaller 2.5V photodiode detector response is captured 40 microseconds later on the capacitor and read by the A/D chip back into the PIC microcontroller.

Figure 29:
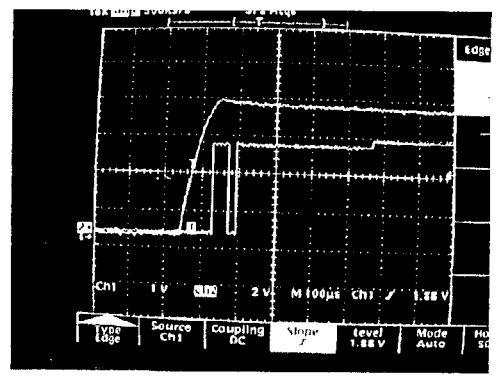

FIG. 29 shows the conversion or translation of the analogue signal, which is the stored charged on the capacitor caused by the photodiode response, into a digital format by a A/D device. The conversion or translation starts when a TTL signal (i.e., the square wave on FIG. 29) occurs, which is approximately 11 microseconds after the peak stored voltage has been reached in the capacitor. The first 40 microsecond pulse followed by a 20 microsecond dip is actually the digital data input in the form of a 3 bit word that configures the Linear Technology 1298 A/D chip to enable the start of the conversion. Such conversion or translation image is captured by an oscilloscope.

Figure 30:
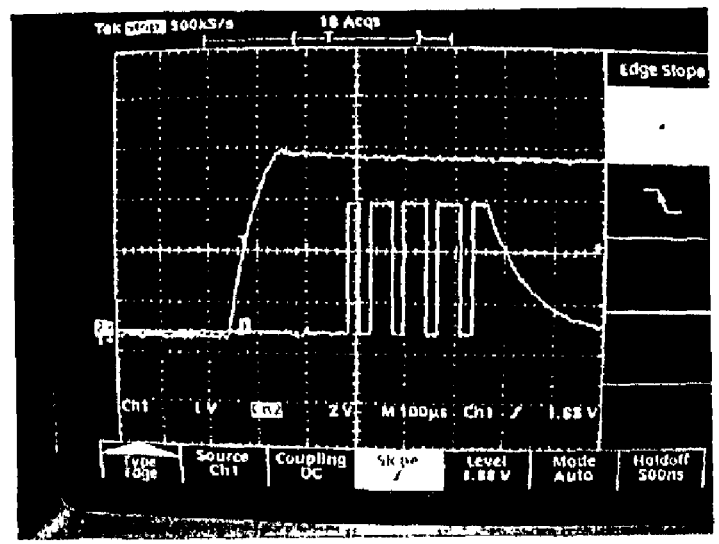

FIG. 30 shows the whole process including the initial signaling, the signal detection, the conversion from analog to digital format, and the outputting of the digital data to the PIC microcontroller, all taking place within 540 microseconds, which is much shorter than the time intervals between signals, as determined by the repetition rate of the flash lamp (usually about 10 Hz). Specifically, the latter three steps (i.e., the signal detection, the conversion, and the data outputting) occur within the time period when the voltage charge is stored on the capacitor.

Figure 31:
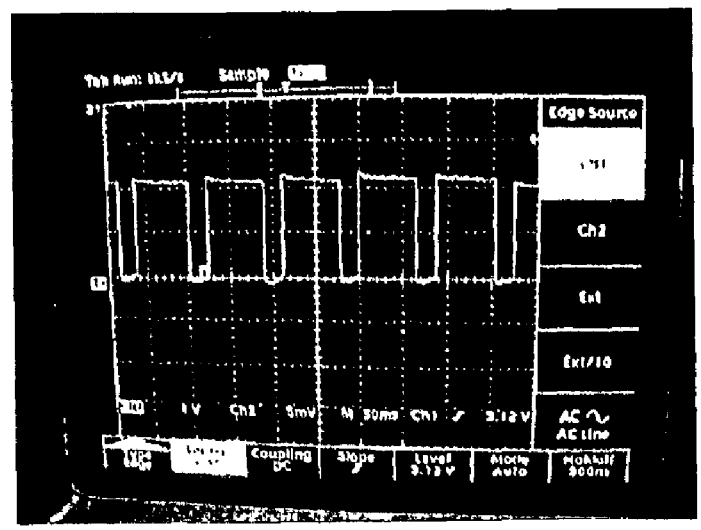

FIG. 31 shows a typical pulse series measured at the capacitor as the output of the operational amplifier U1A. Within each pulse, the process illustrated in FIG. 28 occurs, which includes the charging of the capacitor upon detection of the flash UV light by the photodiode, the reading of the stored charge, the conversion of the charge data into a digital format, the transmission of such digital data into the PIC microcontroller, and the discharging of the capacitor after the data has been read. The pulse frequency is approximately 800 milliseconds or 12.5 Hz.

With regard to UV light detector, conventional SiC photodiodes generate weak current signals that are susceptible to environmental noise, and a significant portion of the signal may be lost due to the low signal to noise ratio. In order to solve such problems of the conventional SiC photodiodes, the present invention employs a hybrid photodiode or a photodiode equipped with an integrated operational amplifier, so as to minimize signal interference. Preferably, a hybrid photodiode, such as a UV enhanced silicon photodiode in a standard TO5 package, allows for an extremely robust signal prior to any amplification and generates stable pulse peak heights of smaller variance.

Figure 32:
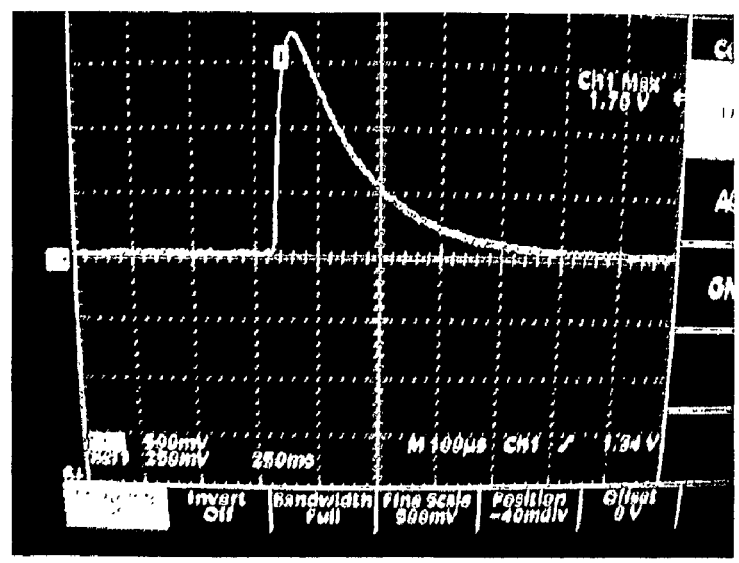
FIG. 32 shows a raw signal outputted by a UV enhanced silicon hybrid photodiode.

FIG. 32 shows a raw signal from the UV enhanced silicon photodiode as described hereinabove, in a sample cell containing air only and measured by an oscilloscope. The magnitude of the raw signal is greater than 1.7 volts, without any amplification, and the FWHM is approximately 120 microseconds. This signal is significantly better than that measured by the conventional SiC photodiode, which could not be measured without at least one stage of amplification by the photometer board. The strong signal seen above indicates that the signal-to-noise ratio will no longer be an issue.

Optical Cell for Conducting Spectrometry

The present application in another aspect relates to an optical cell for conducting spectrometric analysis of a target component, such as the brightener or the antioxidant, contained by a sample solder plating solution.

Such optical cell may comprises:

a first fluid compartment of a first volume;

one or more fluid inlets connected to the first fluid compartment for introducing one or more test solutions thereinto;

a second fluid compartment of a second volume connected to the first fluid compartment, wherein the second volume is smaller than the first volume;

a fluid outlet connected to the second fluid compartment for discharging one or more test solutions;

optionally, a fluid mixing device in the first and/or second fluid compartment for mixing the one or more test solutions;

an irradiation light source for irradiating light into the second fluid compartment;

a light detector coupled with the irradiation light source for detecting light transmitted or emitted by the one or more test solutions in said second fluid compartment; and optionally, a computational device connected with the light detector, for collecting absorbance spectrum of the one or more test solutions and conducting spectrometric analysis based thereon.

Figure 33:
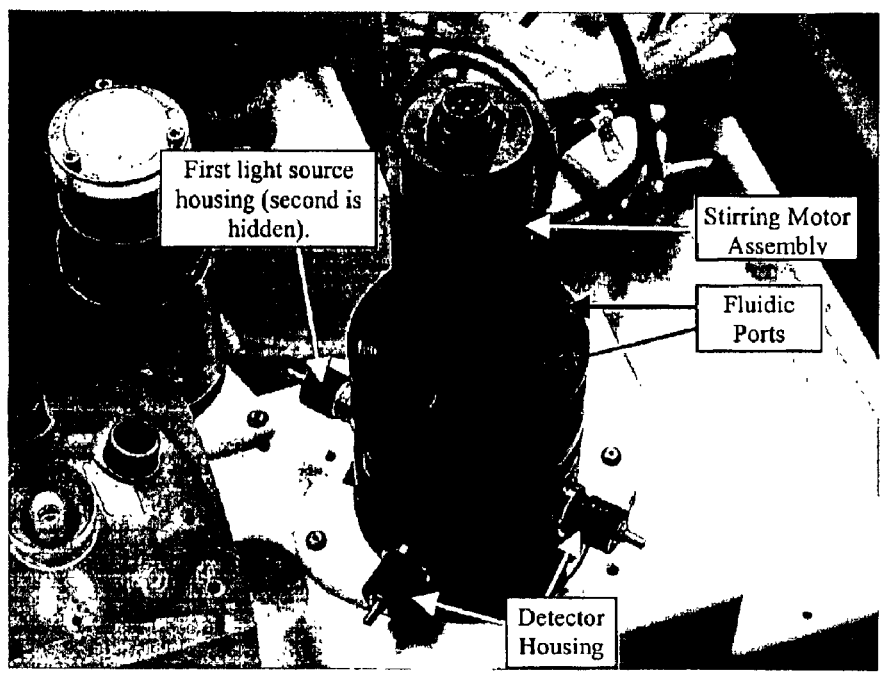
FIGS. 33 and 33A–33C show various views of an optical cell according to one embodiment of the present invention.

FIG. 33 shows an exterior view of an optical cell according to one embodiment of the present invention, having two light source housings, two detecting housings, a stirring motor assembly, and eight fluidic ports for introducing test solutions.

Figure 33A:
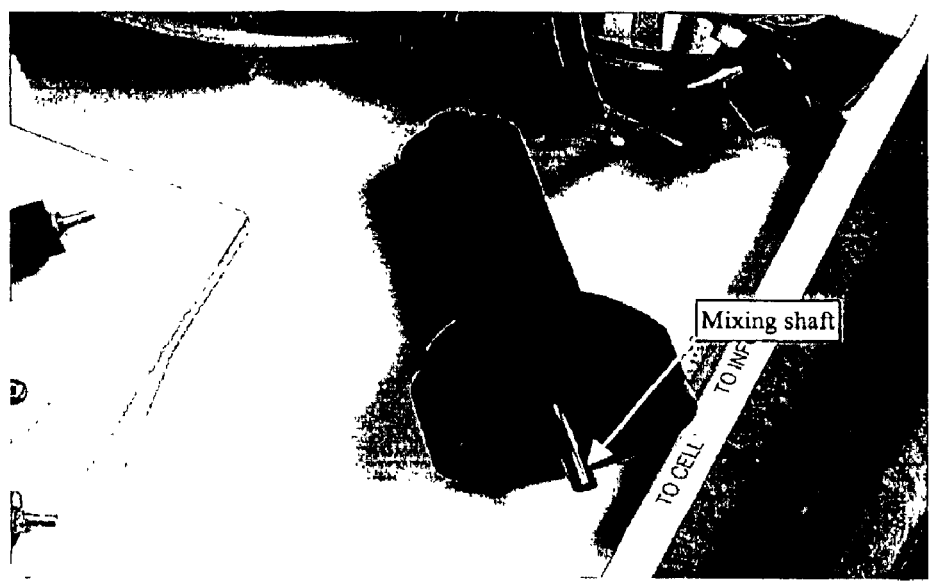

FIG. 33A shows the top half of the optical cell, comprising a cap and a mixing shaft for mixing the test solutions.

Figure 33B:
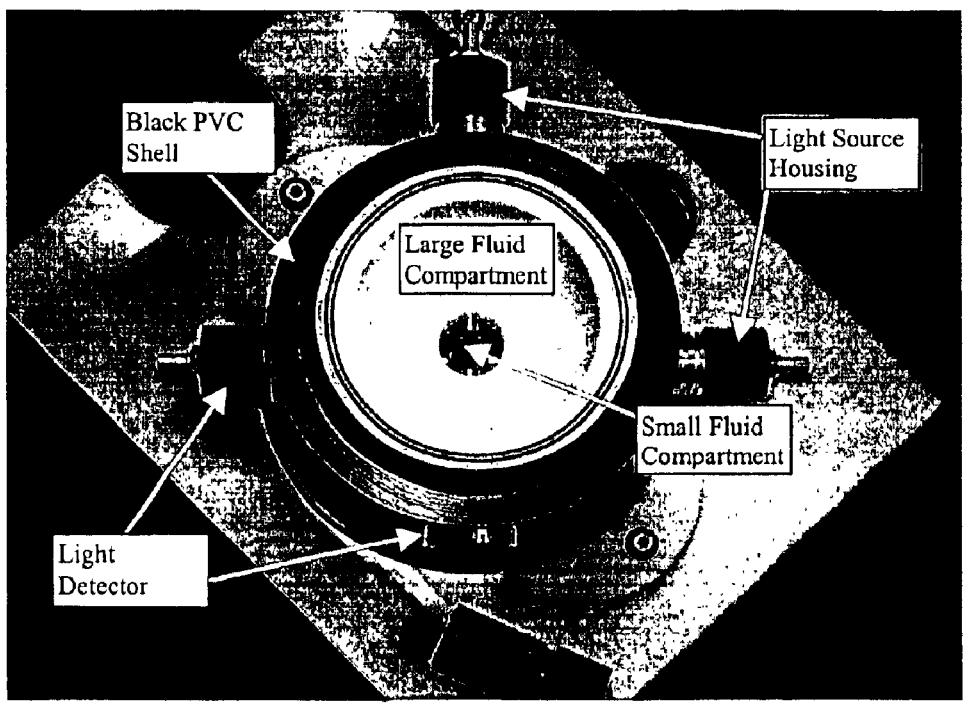
Figure 33C:
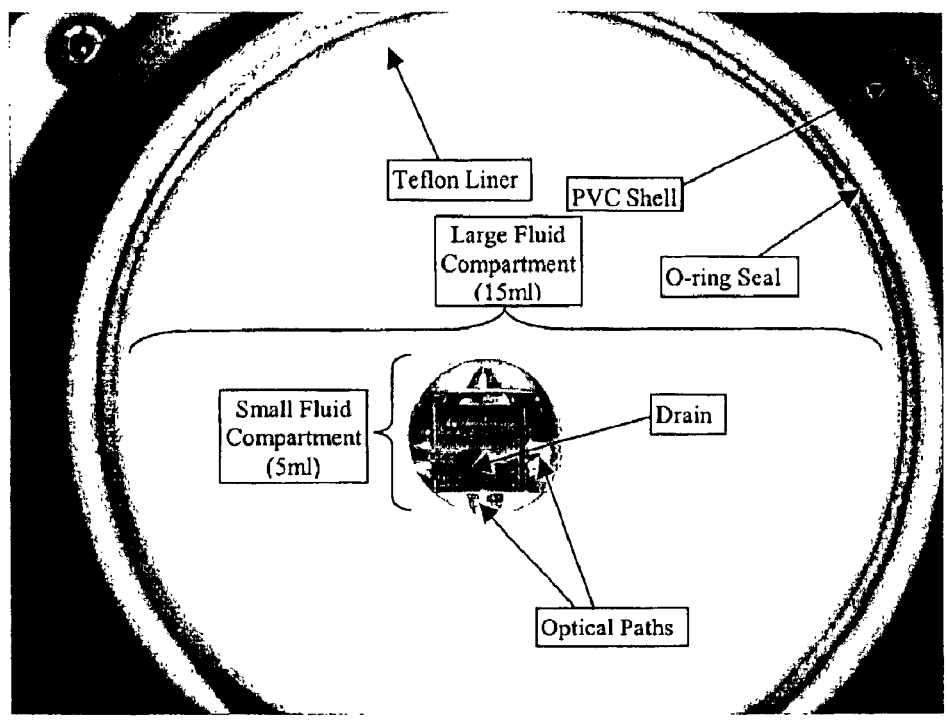

FIGS. 33B and 33C shows the cross-sectional views of the bottom half of the optical cell, comprising a large fluid compartment and small fluid compartment connected thereto. Preferably, the small fluid compartment has a volume of about ⅕ to about ½ of that of the large fluid compartment. The light source and the light detector are arranged and constructed to provide one or more light paths through such small fluid compartment for spectrometric analysis. The fluidic ports are connected to the large fluid compartment for introducing one or more test solutions thereinto, and the mixing shaft extends through the whole large fluid compartment into the small fluid compartment and terminates above where the light paths are. Therefore, the large fluid compartment provides a sufficiently large space for fluid introduction and mixing, without obstructing the light paths or otherwise interfering with the spectrometric analysis in the small fluid compartment. Such double-compartment configuration for the optical cell requires a minimum amount of sample solder plating solution to be used for analysis purpose, as determined by the volume of the small fluid compartment, instead of that of the large fluid compartment.

Since the antioxidant component of solder plating solution is light-sensitive, the present invention provides an opaque polymeric cover for covering both the large and the small fluid compartments. Such opaque polymeric cover is preferably a black polyvinyl chloride cover. Moreover, since the solder plating solution is highly corrosive, the optical cell of the present invention preferably comprises a corrosion-resistant liner on the interior surface of each of the large and the small fluid compartments. Such corrosion-resistant liner is more preferably a tetrafluoroethylene liner, and most preferably a Teflon® liner.

Figure 34:
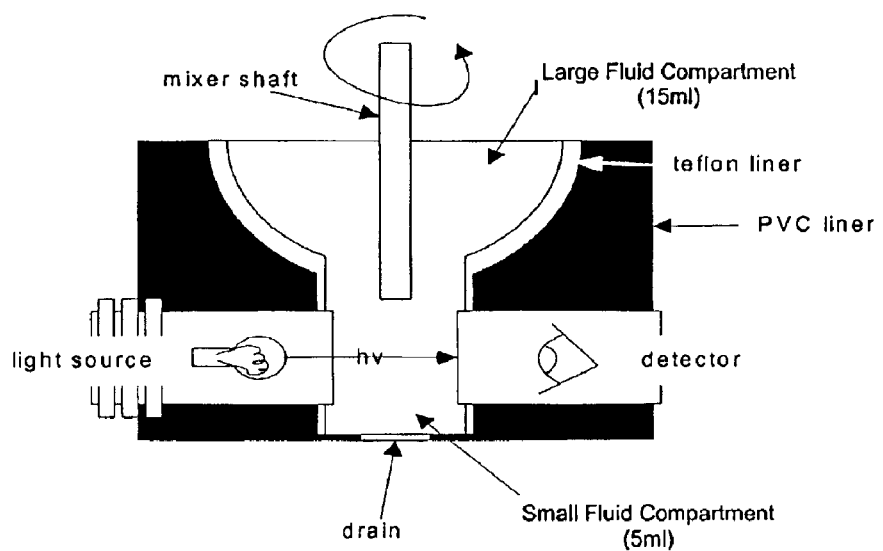
FIG. 34 shows a schematic view of the optical cell of FIGS. 33–33C.

FIG. 34 shows a perspective view of the optical cell of the present invention, wherein a light source directs light through the small fluid compartment into a light detector, for conducting spectrometric analysis.

A computation device (not shown here) can further be provided, which connects to the light detector for collecting absorbance spectrum of said one or more test solutions and conducting spectrometric analysis based thereon. Said computation device may comprise personal computers, work stations, microprocessors, on-line analyzer, or any other suitable computation devices.

Raman Spectroscopic Measurements

Raman spectroscopy is a non-destructive, quantitative, and qualitative tool used for the identification and analysis of both inorganic and organic species. It has been widely considered a complementary analysis method to infrared spectroscopy. A significant advantage that Raman spectroscopy possesses over infrared spectroscopy is the ability to collect useful molecular information under aqueous conditions using sample cells made of glass or quartz.

Instrumentation for Raman spectroscopy comprises three major components: a high-intensity irradiation source, a sample illumination system, and a spectrophotometer.

Irradiation sources that have been used for Raman spectroscopy range from HeNe lasers to Nd:YAG lasers. The choice of laser used for the analysis is largely determined by the method of analysis and molecular species.

Sample illumination can be achieved using a number of techniques. With the advancement of fiber optic technology, great variability in cell design can be achieved.

The Raman spectroscopy system can be incorporated into an analyzing cell that is designed for analyzing solder plating solutions, which allows continuous flow of sample solder plating solutions therethrough and offers real-time, in situ analysis of the sample solution. The analyzing cell also comprises inlet and outlet valves, so that such cell can be isolated from the sample flow during calibration or cleaning process.

Because Raman spectrophotometer detects the amount of radiation energy scattered by a specific component of the solder plating solution, and because the intensity of such scattered radiation energy is linearly proportional to the concentration of the specific component, Raman spectroscopy can be used to accurately and precisely determine the concentrations of various components, including inorganic or organic components, in solder plating solutions.

Overall, Raman spectroscopy provides efficient concentration determination method for solder plating solutions, or other type of metal plating solutions. Moreover, the recent availability of spectral database make it possible to perform spectral searches using obtained spectral data, therefore, spectra of multiple components in a sample solution can be separated, and impurities or by-products in such sample solution can be readily determined.

Although the invention has been variously disclosed herein with reference to illustrative embodiments and features, it will be appreciated that the embodiments and features described hereinabove are not intended to limit the scope of the invention, and that other variations, modifications and other embodiments will suggest themselves to those of ordinary skill in the art. The invention therefore is to be broadly construed, consistent with the claims hereafter set forth.

What is claimed is:

1. A method for determining tin concentration in a sample solder plating solution comprising tin and lead ions, by titrating said sample solder plating solution with a titration solution that comprises a material selected from the group consisting of iodine and iodide, and by measuring reduction-oxidation potential responses of said sample solder plating solution, during the titration, said method comprising the steps of:

(a) adding a stabilizing solution into the sample solder plating solution, for stabilizing the lead ions therein to prevent precipitation of said lead ions during subsequent titration;

(b) titrating the sample solder plating solution with the titration solution comprising iodine;

(c) monitoring oxidation-reduction potential of the sample solder plating solution during the iodine titration by using an oxidation-reduction potential electrode, for determining an end point of said titration; and (d) calculating the tin concentration in the sample solder plating solution, based on the titration end point determined in step (c), wherein the oxidation-reduction potential electrode comprises dual polarized platinum electrodes.

2. A method for determining lead concentration in a sample solder plating solution that comprises tin and lead ions, comprising the steps of:

(a) determining the total metal concentration in said sample solder plating solution;

(b) determining the tin concentration in said sample solder plating solution, by titrating said sample solder plating solution with a titration solution that comprises a material selected from the group consisting of iodine and iodide, and by measuring reduction-oxidation potential responses of said sample solder plating solution during the titration;

(c) calculating the lead concentration in said sample solder plating solution, by subtracting the tin concentration from the total metal concentration.

3. The method of claim 2, wherein the total metal concentration in said sample solder plating solution is determined by a titration method, which comprises the steps of:

(a) adding excess amount of complexing agent into the sample solder plating solution, so that metal ions in said sample solution form complexes with the complexing agent;

(b) titrating the sample solution with a titration solution, for consuming the excess complexing agent not complexed with the metal ions in the sample solder plating solution;

(c) monitoring the titration process for determining a titration end point, wherein amount of titration solution used for reaching such titration end point is recorded; and (d) calculating the total metal concentration in the sample solder plating solution, based on the amount of complexing agent added into the sample solution and the amount of titration solution used for consuming the excess complexing agent therein.

4. The method of claim 3, wherein the sample solder plating solution is diluted before the complexing agent is added.

5. The method of claim 3, wherein the complexing agent comprises ethylenediaminetetraacetate (EDTA).

6. The method of claim 5, wherein ammonia acetate is used in combination with said complexing agent for adjusting pH value of the sample solder plating solution to above about 4.

7. The method of claim 5, wherein the titration solution comprises copper sulfate, for consuming the excess EDTA not complexed with the metal ions in the sample solder plating solution.

8. The method of claim 7, wherein the titration is monitored by using an ion selective electrode selected from the group consisting of cadmium ion selective electrodes and calcium ion selective electrodes.

* * * * *